(12) United States Patent
Kuroda et al.

(10) Patent No.: US 8,517,929 B2
(45) Date of Patent: Aug. 27, 2013

(54) ENDOSCOPE SYSTEM

(75) Inventors: Osamu Kuroda, Kanagawa (JM);
Takayuki Iida, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 181 days.

(21) Appl. No.: 13/166,765

(22) Filed: Jun. 22, 2011

(65) Prior Publication Data
US 2011/0319712 A1 Dec. 29, 2011

(30) Foreign Application Priority Data

Jun. 28, 2010 (JP) ................ P2010-146865

(51) Int. Cl.
*A61B 1/06* (2006.01)
*A61B 1/04* (2006.01)

(52) U.S. Cl.
USPC ........................................ 600/160; 600/109

(58) Field of Classification Search
USPC .................. 600/103, 109, 160, 176–178, 182
See application file for complete search history.

(56) References Cited

U.S. PATENT DOCUMENTS

| | | | | |
|---|---|---|---|---|
| 5,434,669 A | * | 7/1995 | Tabata et al. | 356/477 |
| 6,993,167 B1 | * | 1/2006 | Skladnev et al. | 382/128 |
| 2003/0120156 A1 | | 6/2003 | Forrester | |
| 2006/0235277 A1 | | 10/2006 | Ohkubu et al. | |
| 2007/0253033 A1 | | 11/2007 | Johansen et al. | |
| 2009/0306478 A1 | * | 12/2009 | Mizuyoshi | 600/178 |
| 2010/0097680 A1 | * | 4/2010 | Naftali et al. | 359/205.1 |
| 2010/0210911 A1 | * | 8/2010 | Shimotsu | 600/178 |
| 2010/0238374 A1 | * | 9/2010 | Ohse | 349/61 |
| 2010/0268034 A1 | * | 10/2010 | Krattiger | 600/178 |
| 2010/0280315 A1 | * | 11/2010 | Pan | 600/109 |
| 2011/0170173 A1 | * | 7/2011 | Mizushima et al. | 359/328 |

FOREIGN PATENT DOCUMENTS

| | | |
|---|---|---|
| JP | 2005-205195 A | 8/2005 |
| JP | 2010-42153 A | 2/2010 |
| JP | 2010-172651 A | 8/2010 |

OTHER PUBLICATIONS

Extended European Search Report of Nov. 14, 2011 citing documents filed in the Jan. 23, 2012 Information Disclosure Statement.

* cited by examiner

*Primary Examiner* — Philip R Smith
(74) *Attorney, Agent, or Firm* — McGinn IP Law Group, PLLC

(57) ABSTRACT

An endoscope system is able to stably obtain an image free from speckle interference. A captured image including a first basic color component B on which a speckle noise of a laser beam is superimposed and a second basic color component G not including the speckle noise. A speckle noise component Bs is extracted based on difference information between the first basic color component B and the second basic color component G Based on the extracted speckle noise component Bs, the speckle noise component Bs is removed from the first basic color component B, so as to obtain a good observation image free from the speckle noise.

8 Claims, 15 Drawing Sheets

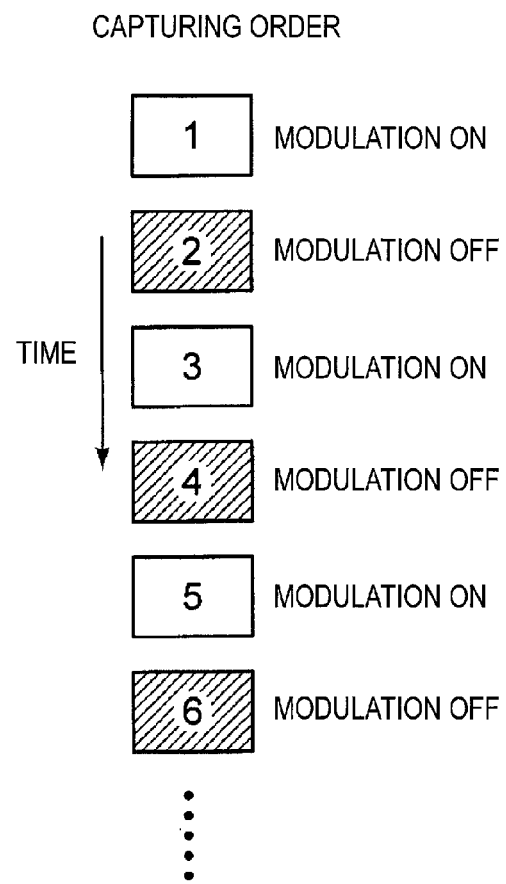
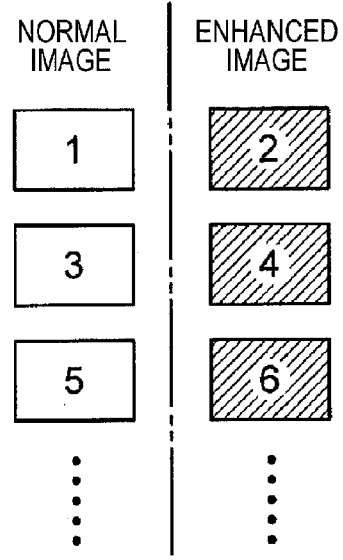
FIG. 14A  FIG. 14B
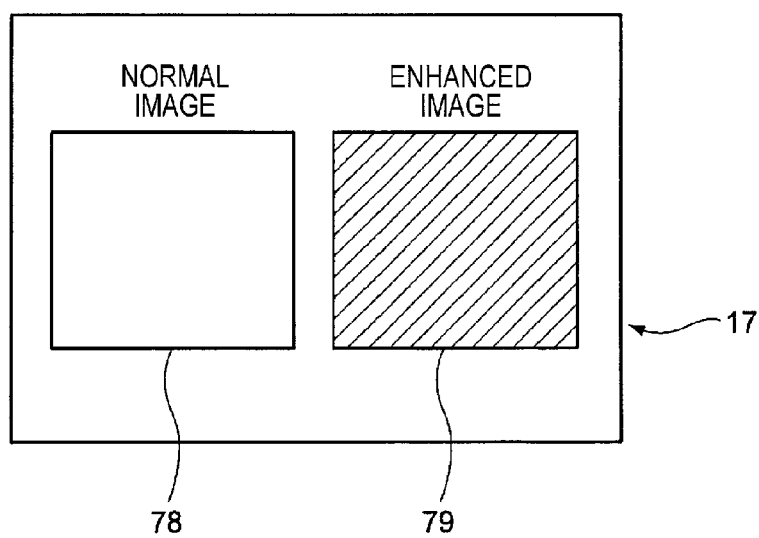
FIG. 15

ENDOSCOPE SYSTEM

CROSS-REFERENCE TO RELATED APPLICATIONS

This application claims the benefit of Japanese Patent Application No. 2010-146865, filed Jun. 28, 2010, the entire contents of which are hereby incorporated by reference, the same as if set forth at length.

BACKGROUND OF INVENTION

1. Field of the Invention

The present invention relates to an endoscope system.

2. Description of the Related Art

In an endoscope system widely used, light emitted from a lamp provided in a light source device is guided by a light guide provided along an endoscope inserting section, and illumination light thus guided by the light guide is emitted through an illumination window disposed at a tip of the endoscope inserting section for irradiating an examination target site. On the contrary, a laser light source is used instead of the lamp for the illumination in some endoscope systems. For example, in a lighting apparatus described in JP 2005-205195 A, light emitted from a blue semiconductor laser is guided to a tip of an endoscope inserting section through an optical fiber for exciting a phosphor disposed at a tip of the optical fiber to emit light, so that white illumination light thus obtained illuminates an examination target site. This lighting apparatus may attain both the required narrowness of the light guide of the endoscope and the brightness of the illumination light.

It is known, however, that intensity noises such as a hopping mode noise, a return light noise and a speckle noise on an irradiated face are caused in using a semiconductor laser. As described in JP 2005-205195 A, when a semiconductor laser is used, such a phenomenon occurs that a noise pattern in the form of spots fluctuation on an irradiated face depending on an irregular shape of the irradiated face. This fine fluctuation is caused due to speckle interference. Since such fine fluctuation may be an obstacle to observation of a diseased part when the illumination light is used in an endoscope or the like, a technique to prevent the fluctuation is now being studied.

SUMMARY OF INVENTION

The invention has been made in view of the above circumstances, and the invention provides an endoscope system capable of always stably obtaining an image free from speckle interference.

According to aspect of the invention, an endoscope system captures an image of a subject under illumination light including a laser beam by an imaging device having sensitivities to a plurality of basic color components. The endoscope system performs image processing for the captured image and outputs the resultant image as an observation image. The captured image includes a first basic color component on which a speckle noise of the laser beam is superimposed and a second basic color component not including the speckle noise. The endoscope system includes a speckle noise extracting unit and a controller. The speckle noise extracting unit extracts a speckle noise component based on difference information between the first basic color component and the second basic color component. The controller that determines a control amount for removing the speckle noise component from the first basic color component based on the extracted speckle noise component.

In the endoscope system, the speckle component is extracted based on the difference information between the first basic color component and the second basic color component, so as to remove the speckle noise by using this speckle component as an evaluation parameter. Therefore, by perform the control using the evaluation parameter with respect to the speckle noise, which has been difficult to quantitatively evaluate, a control amount for removing the speckle noise can be optimally set. Accordingly, it is not necessary to perform useless control or excessive calculation for removing a speckle noise, and hence, the speckle noise can be appropriately removed with high efficiency. As a result, an observation image free from fluctuation and unevenness peculiar to laser can be always stably obtained.

BRIEF DESCRIPTION OF THE DRAWINGS

FIG. 14A is an explanatory diagram of a plurality of frame images obtained in a time series by capturing by an imaging optical system, FIG. 14B is an explanatory diagram conceptually illustrating classification of the frame images, FIG. 15 is an explanatory diagram showing a state in which, an image obtained under illumination of white light including little speckle noise and an image obtained under illumination of white light including much speckle noise are displayed in different display areas in a display screen of a monitor.

DESCRIPTION OF EXEMPLARY EMBODIMENTS

Embodiments of an endoscope system of this invention will now be described in detail with reference to the accompanying drawings. First, the configuration of an endoscope will be described.

(First Configuration)

Figure 1:
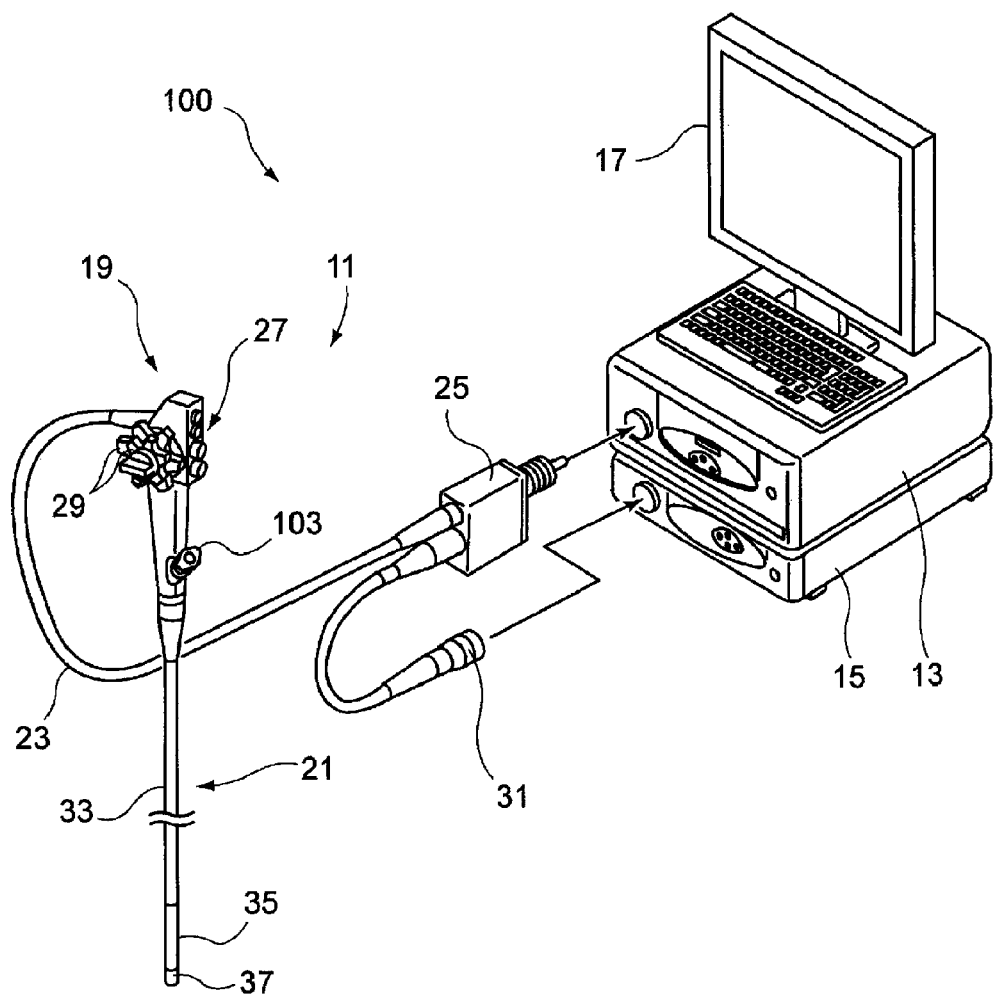
FIG. 1 is a diagram explaining an embodiment of the invention, and specifically is a schematic diagram of an endoscope system illustrating an endoscope and various devices connected to the endoscope.
Figure 2:
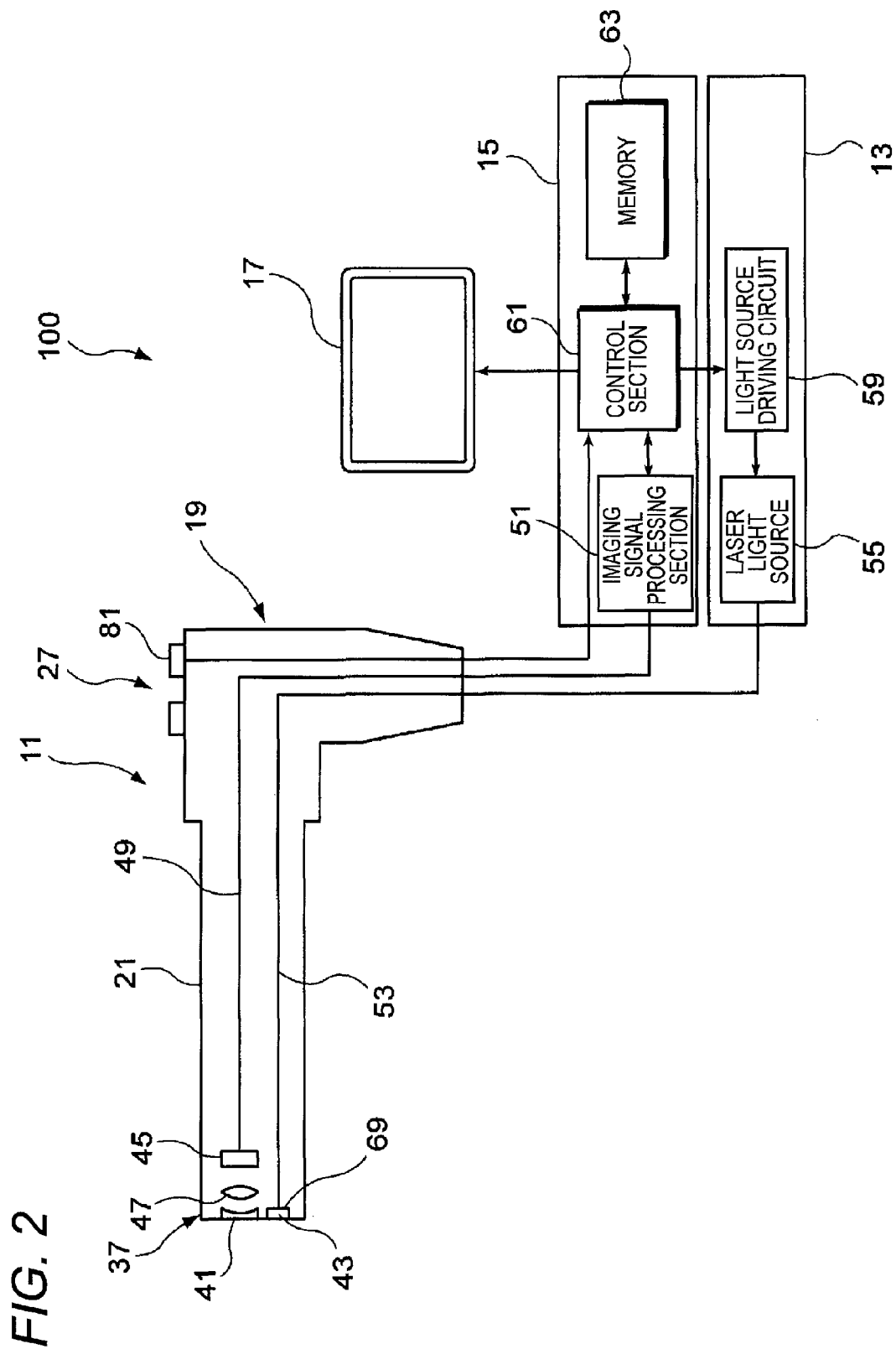
FIG. 2 is a block diagram of the endoscope system.

FIG. 1 is a schematic diagram of the endoscope system for illustrating an endoscope and respective devices connected to the endoscope, and FIG. 2 is a block diagram of the endoscope system of FIG. 1.

As illustrated in FIG. 1, the endoscope system 100 includes the endoscope 11, a light source device 13, a processor 15 for performing imaging signal processing and a monitor 17. The endoscope 11 includes an operating section 19 and an inserting section 21, which is connected to the operating section 19 and is inserted into a subject (a body cavity). The operating section 19 is connected to a universal cord 23, and a tip of the universal cord 23 is connected to the light source device 13 through a light guide (LG) connector 25. Furthermore, an imaging signal is input to the processor 15 through a video connector 31.

In the operating section 19 of the endoscope 11, various operation buttons 27 such as those for conducting suction, air supply and water supply on the tip side of the inserting section 21 and a shutter button to be used in imaging are arranged. A pair of angle knobs 29A and 29B are provided. The inserting section 21 includes a soft part 33, a bending part 35 and a tip part 37 successively disposed in this order from the side of the operating section 19. The bending part 35 is remotely controlled to be bent by rotating the angle knobs 29A and 29B of the operating section 19. As a result, the tip part 37 can be made to face toward a desired direction.

Moreover, as illustrated in FIG. 2, on the tip part 37 of the endoscope 11, an observation window 41 of an imaging optical system and a light emission window 43 of an illumination optical system are disposed, so that reflection light of illumination light emitted through the light emission window 43 and reflected on a subject is captured through the observation window 41. An observation image thus obtained is displayed on the monitor 17 connected to the processor 15.

The imaging optical system includes an imaging device 45 such as a CCD (charge coupled device) or a CMOS (complementary metal-oxide semiconductor), and an optical member such as a lens 47. An observation image acquired by the imaging optical system forms an image on a light receiving surface of the imaging device 45 so as to be converted into an electric signal. The electric signal is input to an imaging signal processing section 51 of the processor 15 through a signal cable 49 so as to be converted into a video signal therein.

The illumination optical system (an example of a lighting apparatus) includes the light source device 13 having a laser light source section 55, an optical fiber 53 connected to the light source section 13, and a phosphor 69 serving as a wavelength converting section and disposed on the light emitting side of the optical fiber 53. The optical fiber 53 is an optical fiber cable including a core layer at the center thereof and a clad layer disposed around the core layer. The optical fiber 53 guides a laser beam to the tip part 37 of the endoscope 11 so as to allow the phosphor 69 disposed in the tip part 37 to emit white illumination light. The laser light source section 55 receives a driving signal, which is input from a light source driving circuit 59 based on a command issued by a control section 61, and emits a laser beam.

The control section 61 is connected to a memory 63 for storing the imaging signal. The control section 61 controls the whole of the endoscope system 100 so as to display image data output from the imaging signal processing section 51 on the monitor 17 and to connect with a network such as a LAN not shown for delivering information including the image data.

The laser light source section 55 includes a blue semiconductor laser that generates a blue laser beam of a wavelength of 445 nm, that is, light of a first wavelength band. As the blue semiconductor laser, a broad-area type InGaN-based laser diode may be used, or an InGaNAs-based laser diode or a GaNAs-based laser diode may be used.

The blue laser beam emitted from the laser light source section 55 (that is, the blue semiconductor laser) is input to the optical fiber 53 by a condensing lens (not shown) and is propagated to the tip part 37 of the endoscope 11, excites the phosphor 69 serving as the wavelength converting section for emitting fluorescence, that is, light of a second wavelength band. Also, a part of the blue laser beam passes through the phosphor 69 as it is.

The phosphor 69 includes a plurality of kinds of phosphors (such as a YAG-based phosphor and a phosphor of BMA ($BaMgAl_{10}O_{37}$) or the like) that absorb a part of the blue laser beam and emit light of green to yellow through the excitation. As a result, the excitation light of green to yellow obtained from the blue laser beam and a part of the blue laser beam not absorbed by but passing through the phosphor 69 are combined so as to generate white (pseudo white) illumination light.

Figure 3:
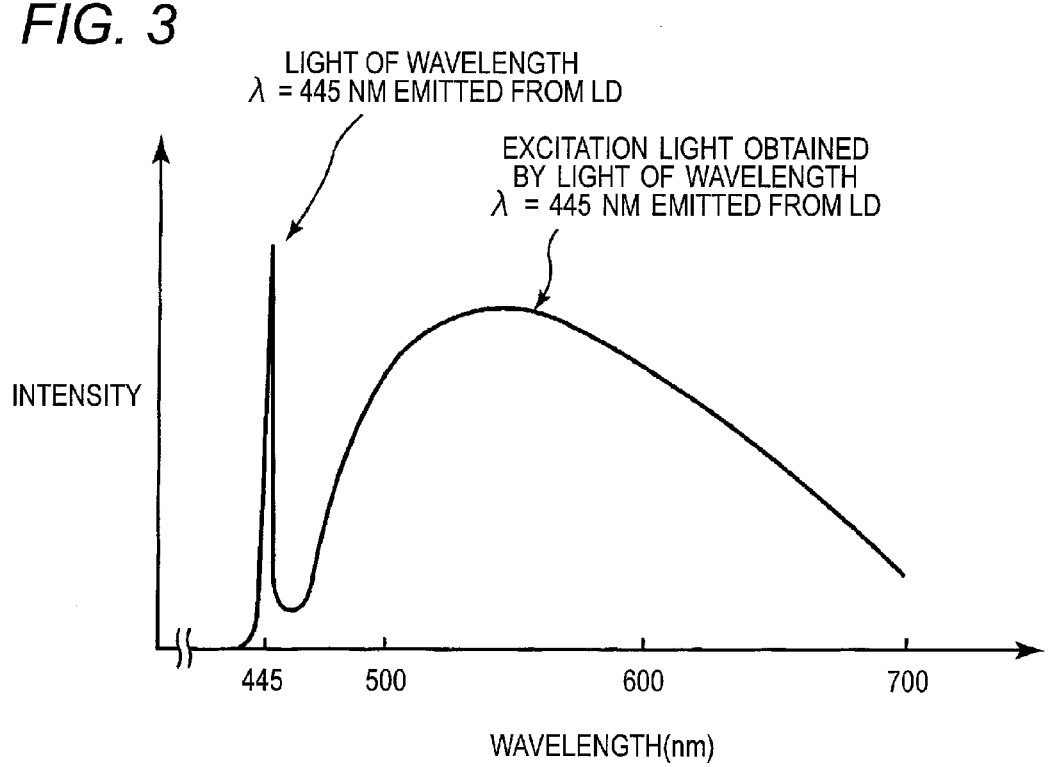
FIG. 3 is a graph of an emission spectrum of a blue laser beam emitted from a blue semiconductor laser and light obtained by converting a wavelength of the blue laser beam by a phosphor.

FIG. 3 is a graph illustrating an emission spectrum of the blue laser beam emitted from the blue semiconductor laser and a spectrum of the light obtained by converting the wavelength of the blue laser beam by the phosphor 69. The blue laser beam (that is, the light of the first wavelength band) is expressed as an emission line having a center wavelength of 445 nm and the excitation emitted light (that is, the light of the second wavelength band) obtained from the blue laser beam and emitted by the phosphor 69 has a spectral intensity distribution having an increased emission intensity in a wavelength band of approximately 450 nm through 700 nm. The profiles of the excitation emitted light and the blue laser beam generate the white illumination light.

The white illumination light is not limited to light strictly including all wavelength components of visible light but may be any light so long as it includes light of specific wavelength bands such as R, G and B. In a broad sense, examples of the white light includes light having wavelength components from green to red, light having wavelength components from blue to green, and the like.

Referring to FIG. 2 again, the white illumination light generated from the blue laser beam and the excitation emitted light from the phosphor 69 as described above illuminates an observed area of a subject through the light emission window 43 provided in the tip part 37 of the endoscope 11. Then, an image of the observed area irradiated with the white illumination light is formed on the light receiving surface of the imaging device 45 by the lens 47, and the image is converted into an electric signal, and the electric signal is input through the cable 49 to the imaging signal processing section 51 of the processor 15, in which the electric signal is converted into a video signal.

It is known that when a semiconductor laser is used, a speckle noise occurs on an irradiated face. It is also known that the speckle noise is noticeable in a multimode optical fiber rather than in a single mode optical fiber.

Figure 4:
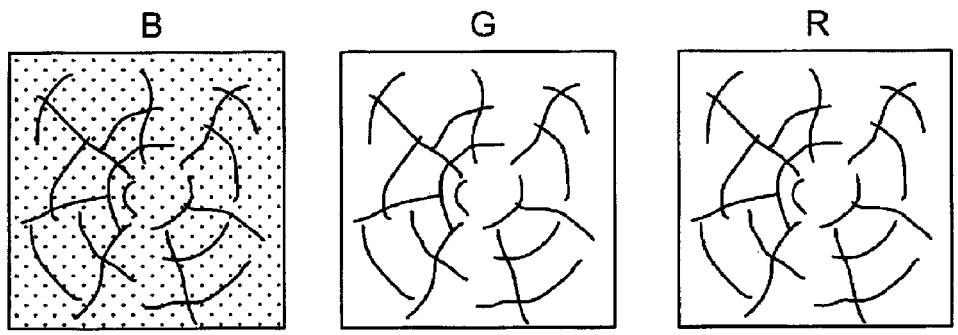
FIG. 4 is an explanatory diagram of captured images obtained by an imaging device having sensitivities to basic color components of BGR.

The imaging device 45 of this configuration has sensitivities to three basic color components of primary colors of red (R), green (G) and blue (B). In captured images, obtained by the imaging device 45, of a subject (for example, a diseased part) irradiated with the white illumination light including the blue laser beam, a shape of the subject is substantially the same among the captured images of the respective color components (of RGB) as illustrated in FIG. 4. In the captured image of the B component (of the first wavelength band) in which a speckle noise component is superimposed, much speckle noise is caused, while such a noise is minimally caused in the captured images of the other color components (i.e., the R and G components). The speckle noise may be an obstacle to observation of the diseased part in the endoscope. Hence, an observation image in which the speckle noise has been removed is desired to be displayed on the monitor 17.

Removal of the speckle noise will now be described.

Figure 5:
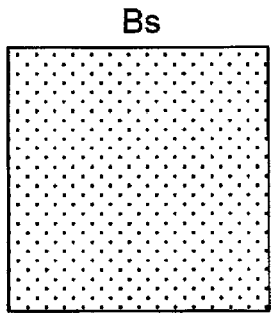
FIG. 5 is an explanatory diagram of a speckle noise component extracted from a B component by a speckle noise extracting unit.

The imaging signal processing section 51 extracts a speckle noise component based on difference information between the B component(an example of a first basic color component) including a speckle noise and the G component (an example of a second basic color component) not including a speckle noise in a captured image obtained by the imaging device 45. Specifically, a speckle noise extracting unit divides the B component of each pixel of the captured image by the G component of each pixel of the captured image, so as to extract pixels whose blue and green components are different, namely, so as to extract brightness change caused by the speckle noise. Thus, a speckle noise component Bs of each pixel is extracted as illustrated in FIG. 5.

Subsequently, the imaging signal processing section 51 subtracts the speckle noise component Bs of each pixel of the captured image from the B component of each pixel, so as to remove the speckle noise component Bs superimposed on the B component. Thereby, a captured image not including the speckle noise component Bs is generated. An observation image in which the speckle noise component Bs has been thus removed is displayed on the monitor 17 (see FIGS. 1 and 2).

In this manner, the imaging signal processing section 51 functions as the speckle noise extracting unit and a controller that performs an operation process. The removal of the speckle noise component Bs is conducted by extracting the speckle noise component Bs from the captured image of the B component and subtracting the speckle noise component Bs from the captured image of the B component. Therefore, the removal of the speckle noise component Bs by this method is more effectively applied to a still image than to a moving image that requires high speed processing.

It is noted that the R component may be used as the second basic color component not including the speckle noise to obtain the speckle noise component Bs based on difference information between the B component and the R component. (Modification 1)

In Modification 1 described below, an imaging device having sensitivities to three basic color components of complementary colors of cyan (C), magenta (M) and yellow (Y) is used for capturing an image.

Figure 6:
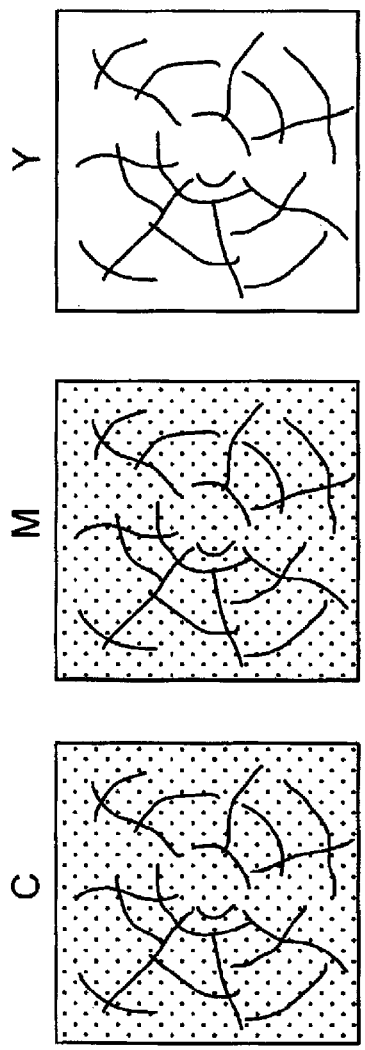
FIG. 6 is an explanatory diagram of captured images obtained by an imaging device having sensitivities to basic color components of CMY.

The imaging device 45 of this modification has sensitivities to the three basic color components of C, M and Y. The color components of C, M and Y are respectively expressed by expressions (1), (2) and (3) below using three basic colors of primary colors RGB. Each of the C component and the M component includes a B (blue) component on which a speckle noise component Bs is superimposed. Therefore, in an image, captured by the imaging device, of a subject under the white illumination light including the laser beam, the speckle noise component Bs is superimposed in the C component and the M component as illustrated in FIG. 6.

$$C=B+G \qquad (1)$$

$$M=B+R \qquad (2)$$

$$Y=G+R \qquad (3)$$

In order to extract the speckle noise component Bs from these C, M and Y basic color components, the imaging signal processing section 51 serves as a color converting unit of the processor 15 obtains, through calculation, a B component and a G component from the C, M and Y components of the captured image in accordance with the following expressions (4) and (5) obtained by transforming the expressions (1) through (3):

$$B=(C+M-Y)/2 \qquad (4)$$

$$G=(C+Y-M)/2 \qquad (5)$$

After the B and the G components are obtained, the imaging signal processing section 51 extracts the speckle noise component Bs of each pixel of the captured image by dividing the B component of each pixel by the G component of each pixel, and thereafter, removes the speckle noise component Bs superimposed on the B component by subtracting the speckle noise component Bs of each pixel from the B component of each pixel. Thus, a Bc (blue) component not including the speckle noise component Bs is obtained.

Thereafter, in order to display an observation image not including the speckle noise component Bs, Cc and Mc components not including the speckle noise component Bs are calculated inversely based on the Bc, R and G components not including the speckle noise component Bs in accordance with the following expressions (6) and (7) (the original Y component is used as it is because the Y component originally does not include the speckle noise component Bs). The thus obtained Cc, Mc and Y components are color-converted into the R, G and B components, so as to generate an observation image as described above, which is displayed on the monitor 17.

$$Cc=Bc+G \qquad (6)$$

$$Mc=Bc+R \qquad (7)$$

(Modification 2)

In Modification 2 described below, an imaging device having sensitivities to four basic color components of C, M, Y and G is used for capturing an image.

Figure 7:
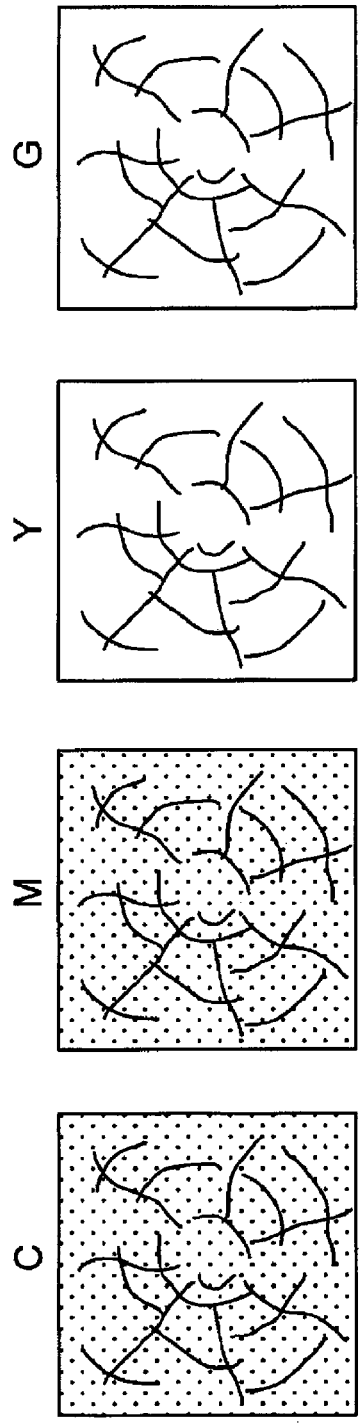
FIG. 7 is an explanatory diagram of captured images obtained by an imaging device having sensitivities to basic color components of CMYG.

The imaging device 45 of this modification has sensitivities to the four basic color components of C, M, Y and G When the imaging device 45 of this modification is used, captured images of C, M, Y and G components are obtained as illustrated in FIG. 7, and a speckle noise component Bs is superimposed on the C and M components as described in Modification 1.

In this modification, B and G components may be obtained in accordance with the expressions (4) and (5) using the C, M and Y components in the same manner as in Modification 1. Since the G component is known, however, a simpler process may be employed in this modification. Specifically, the imaging signal processing section 51 obtains a B component by using the known G component in accordance with the following expression (8):

$$B=C-G \qquad (8)$$

Then, in the same manner as in Modification 1, the imaging signal processing section 51 extracts a speckle noise component Bs of each pixel by dividing the B component of each pixel, which is calculated in accordance with the expression (8), by the known G component of each pixel of the captured image. Furthermore, the speckle noise component Bs superimposed on the B component is removed by subtracting the speckle noise component Bs of each pixel of the captured image from the B component of each pixel. Thus, a Bc component not including the speckle noise component Bs is obtained.

Next, Cc and Mc components not including the speckle noise component Bs are inversely calculated in accordance with the expressions (6) and (7) (the original Y component is used as it is because the Y component originally does not include the speckle noise component Bs). The thus obtained Cc, Mc and Y components are color-converted into R, G and B components so as to generate an observation image as described above, which is displayed on the monitor 17.

(Second Configuration)

Now, a second exemplary configuration of the endoscope system will be described with reference to FIGS. 8 through 15.

In this exemplary configuration, a high frequency signal is superimposed on a driving current for a semiconductor laser of a laser light source section so as to reduce the speckle noise component Bs described above to a target value through feedback control.

As illustrated in a schematic diagram of an illumination optical system of FIG. 8, the laser light source section 55 includes a broad-area type semiconductor laser 65 emitting blue laser of a center wavelength of 445 nm (hereinafter may be referred to as a blue semiconductor laser) and a condensing lens 67 for condensing a laser beam emitted from the blue semiconductor laser 65. In semiconductor lasers, as a wavelength of emitted light is shorter, a width of an active region (a stripe) corresponding to a single mode is smaller. For a blue semiconductor laser, a single mode condition is that the width of the active region be 1 through 2 μm. Accordingly, a semiconductor laser having the active region having a width of 3 through 6 μm or more, which is several times as large as that for the single mode, may be called a broad-area type semiconductor laser. In other words, a broad-area type semiconductor laser is herein defined as a semiconductor laser including an active region having a width of, for example, 3 through 6 μm or more (more specifically, 5 μm or more and 50 μm or less for example), with being distinguished from a narrow stripe type semiconductor laser having a narrow active region.

As far as the wavelength of emitted light is in the 400 nm range (for example, 405 nm or 445 nm), the width may be 50 μm or less as mentioned above from the practical point of view. This upper limit of the width of the active region means, however, that a width of approximately 50 μm is a limit due to the present technique to grow nitride crystal and high non-uniformity in the selected substrate plane direction, and is not a theoretical limit. Some of, for example, arsenic phosphorus-based laser diodes having a wavelength of 780 nm used for blood vessel navigation have an active region width of 200 μm.

A driving circuit for the blue semiconductor laser used in the illumination optical system (an example of the lighting apparatus) having the aforementioned configuration will now be described.

Figure 8:
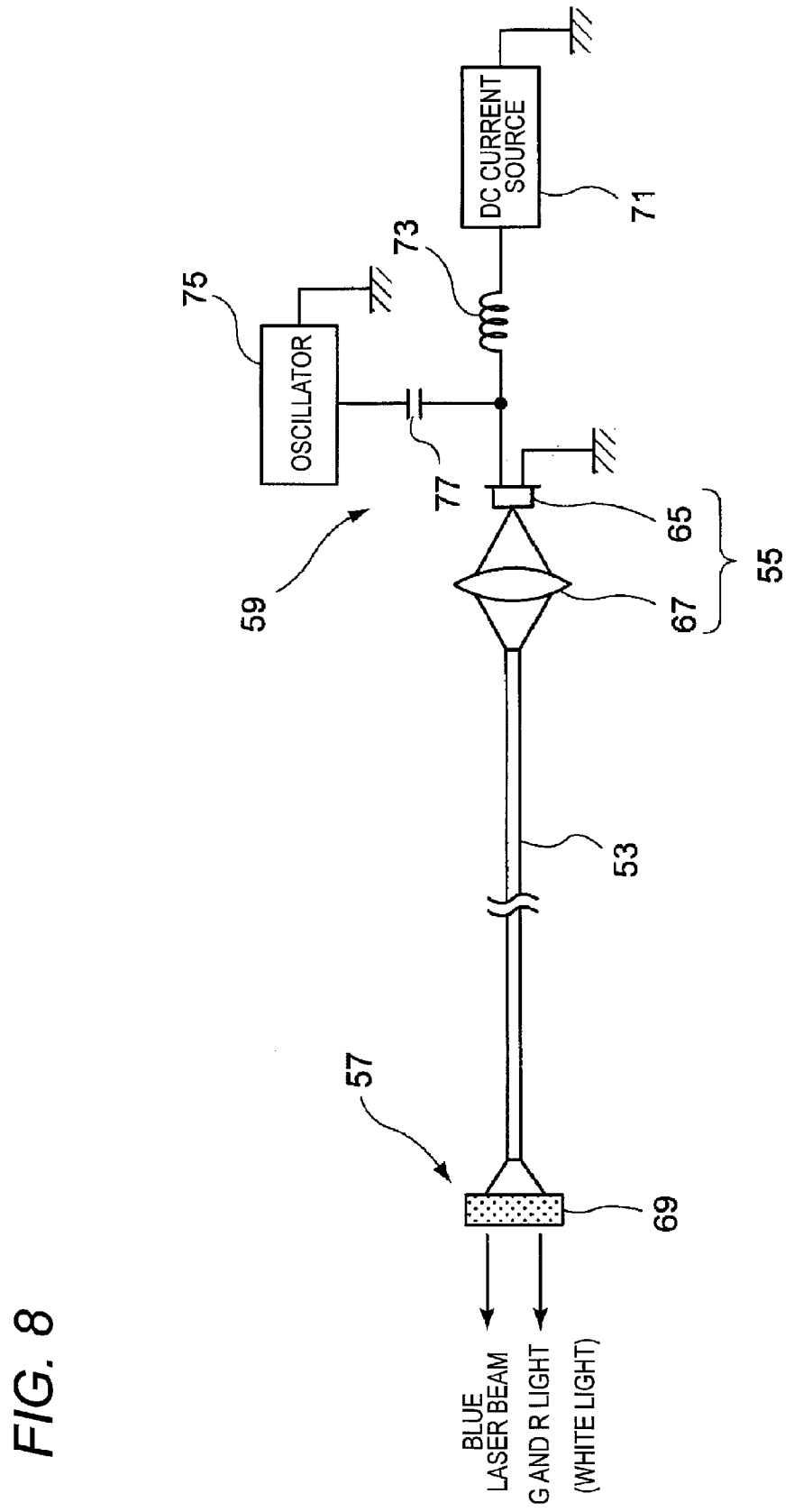
FIG. 8 is a configuration diagram schematically illustrating an illumination optical system of a second configuration.

As illustrated in FIG. 8, the blue semiconductor laser 65 is connected through an inductor 73 to a DC current source 71 for supplying a DC driving current and is also connected through a coupling capacitor 77 to an oscillator 75 for superimposing a sine-wave high frequency signal onto the driving current supplied from the DC current source 71. This high frequency signal is a sine-wave signal that may be arbitrarily set to a frequency of several hundreds through several thousands MHz. When the high frequency signal is superimposed on the driving current, a longitudinal mode of the blue semiconductor laser 65 is changed to multimode. In the aforementioned configuration, the inductor 73 exhibits high impedance with respect to the high frequency signal supplied from the oscillator 75 and exhibits low impedance with respect to the driving current. Also, the coupling capacitor 77 removes a DC component from the high frequency signal supplied from the oscillator 75. In other words, the oscillator 75 functions as a high frequency superimposing unit that causes multimode oscillation of the blue semiconductor laser 65 by superimposing the high frequency signal on the driving current.

Figure 9:
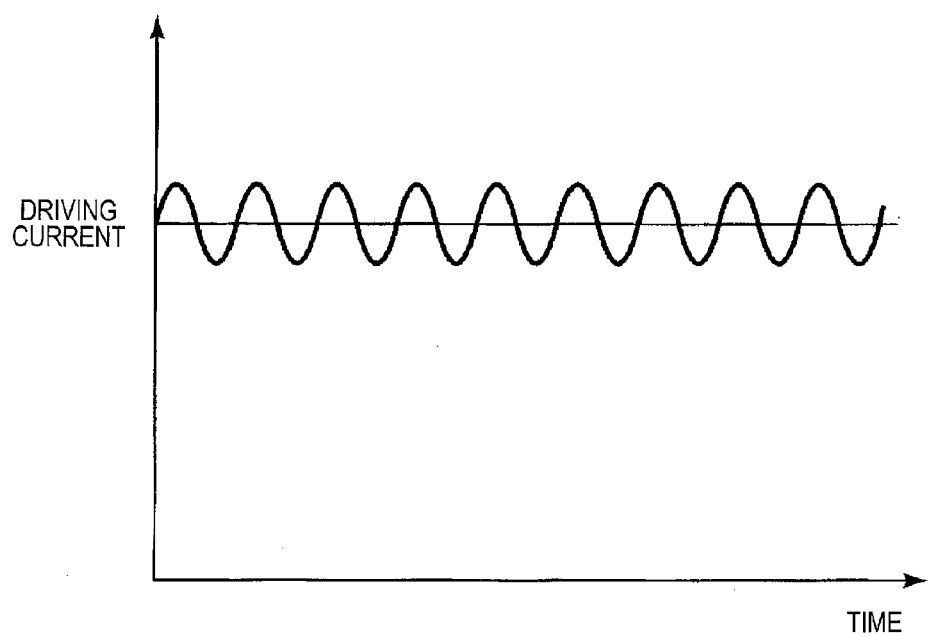
FIG. 9 is a graph illustrating an exemplary driving current provided by a light source driving circuit of FIG. 8.
Figure 10:
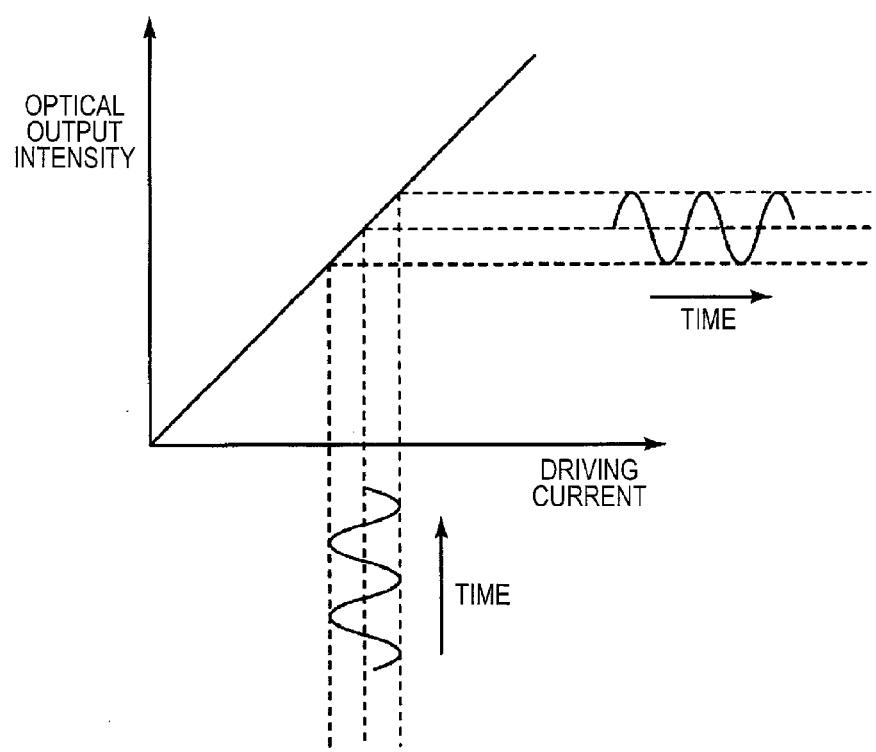
FIG. 10 is a graph illustrating a relationship between a driving current for a blue laser light source and its optical output intensity.
Figure 11:
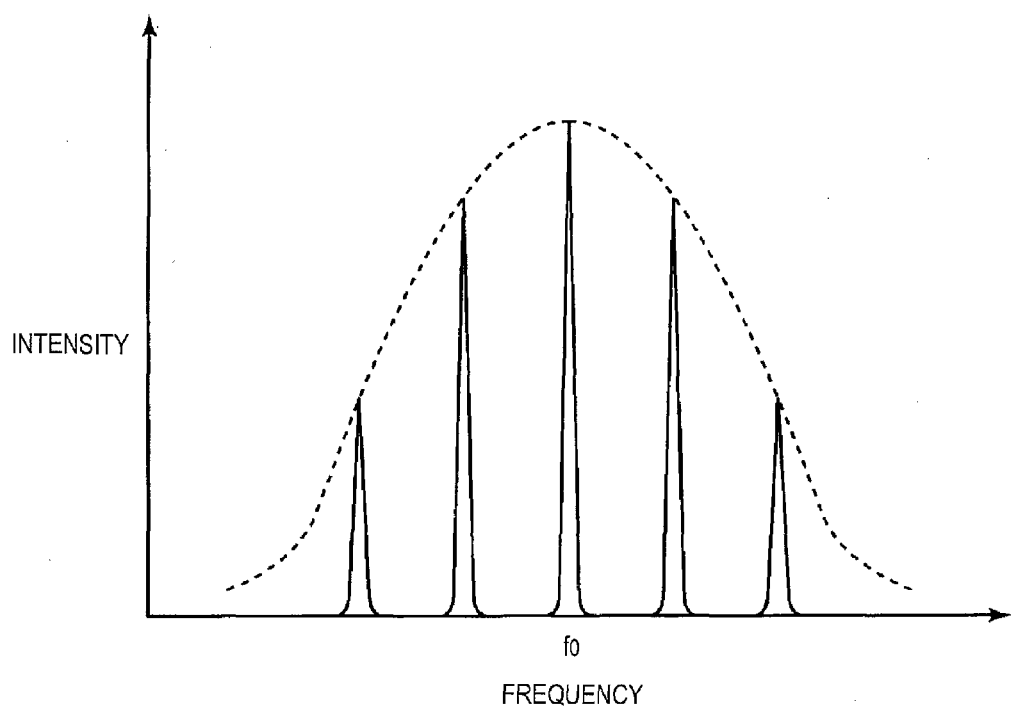
FIG. 11 is a graph illustrating a relationship between a wavelength and an oscillation waveform.

FIG. 9 is a graph illustrating an example of the driving current obtained by the light source driving circuit of FIG. 8, and FIG. 10 is a graph illustrating a relationship between the driving current for the blue semiconductor laser and its optical output intensity.

As illustrated in FIG. 9, in the driving current, the high frequency signal supplied from the oscillator 75 is superimposed on a bias current supplied from the DC current source 71. This driving current is applied to the blue semiconductor laser 65. When the driving current varies as illustrated in FIG. 10, multimode (relaxation oscillation) occurs in transient response of laser oscillation. Hence, the optical output intensity varies. Due to such turbulence with respect to the time axis, coherence is lowered. As a result, occurrence of speckle interference in an area irradiated with the laser beam can be reduced. When this method is employed, no matter whether the blue semiconductor laser 65 has a lateral single mode or a lateral multimode, a speckle noise can be definitely reduced.

Furthermore, a broad-area type semiconductor laser has a large emission width and has a plurality of lateral modes. The respective plural lateral modes have, as illustrated as an oscillation waveform against a wavelength in FIG. 11, different wavelength band components of higher modes having a basic oscillation frequency $f_0$ as its center and has prescribed wavelength distribution. Due to such an increase of the lateral modes and the distribution of the emission wavelengths, the occurrence of speckle interference in an area irradiated with the laser beam can be reduced.

Specifically, by superimposing a high frequency signal, plural lateral modes of blue light emitted from the blue semiconductor laser 65 are disturbed separately with respect to the time axis so as to generate white noise. As a result, the wavelength also varies in accordance with the variation of the lateral modes. Hence, the coherence of the laser beam is lowered. Accordingly, the occurrence of speckle interference may be reduced.

Furthermore, in the case where the laser beam is condensed by the condensing lens 67 onto the optical fiber 53, the respective lateral modes of the broad area type semiconductor laser are different in optical coupling efficiency. The lateral modes may be varied by an external factor such as change in the ambient temperature. At that time, the output of the laser beam would be varied. However, if this configuration is employed, the respective lateral modes are used with being excited evenly. Therefore, even if the lateral mode variation occurs, the variation in the output of the laser beam may be suppressed to be small.

Moreover, in exciting the phosphor, since the lateral modes of the broad-area type semiconductor laser can be modulated by the superimposing the high frequency signal, the output is stabilized with respect to the time axis. Therefore, an intensity noise otherwise occurring at a comparatively low frequency of approximately several kHz can be reduced so that an image can be stably captured.

In this manner, when the driving current on which the high frequency signal is superimposed is applied to the broad-area type blue semiconductor laser 65 having the plural lateral modes, the longitudinal mode is changed to the multimode, each of the plural lateral modes attains wavelength distribution, and the lateral modes are changed with respect to the time axis. Therefore, light minimally causing speckle interference can be always stably emitted. As a result, the speckle noise can be prevented from occurring in an area irradiated with the light.

When the driving current on which the high frequency signal is superimposed is applied to the blue semiconductor laser 65 in the aforementioned manner, the effect to reduce the speckle noise can be attained. When the high frequency signal to superimposed on the driving current is feedback controlled so as to minimize the speckle noise component Bs, the speckle noise may be more effectively reduced.

Figure 12:
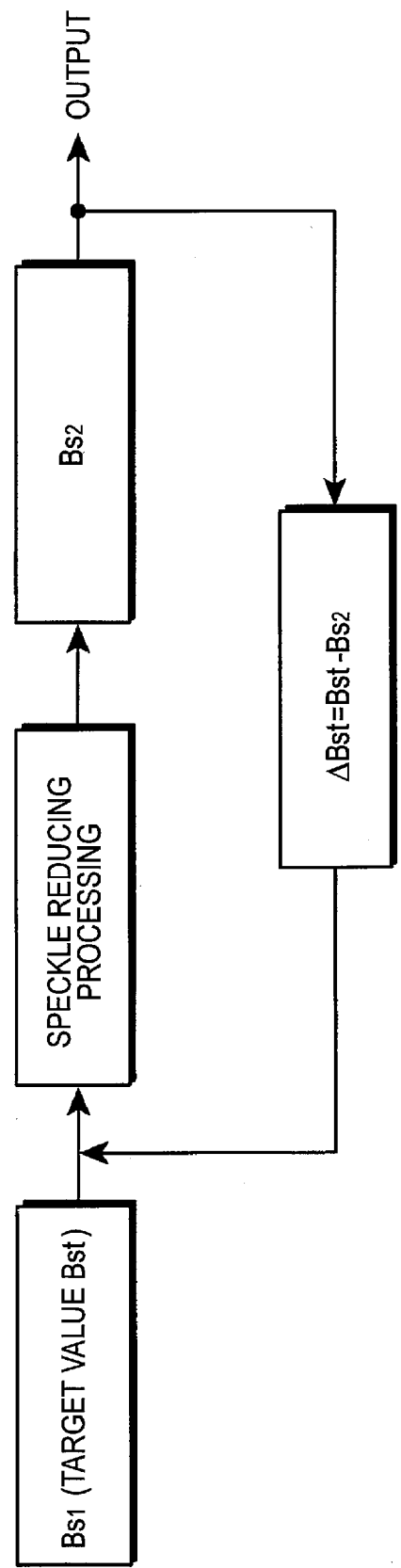
FIG. 12 is a control block diagram of feedback controlling a parameter of a speckle reducing process for minimizing a speckle noise.

FIG. 12 is a control block diagram for feedback-controlling parameters of a speckle reducing process (corresponding to the superimpose of the high frequency signal in this configuration) so as to minimize the speckle noise. As described in the first configuration (see FIGS. 4 and 5), the imaging signal processing section 51 divides the B component of the captured image by the G component of the captured image to obtain a speckle noise component Bs2 after the speckle noise reducing processing for applying the high frequency signal to the driving current for the blue semiconductor laser 65 is performed. Then, based on a difference (ΔBst) between a target speckle noise component Bst and the speckle noise component Bs2, parameters (such as a frequency and an amplitude) of the high frequency signal to be applied to the driving current are feedback controlled so as to minimize the target speckle noise component Bst. Thus, the effect to reduce the speckle noise can be enhanced, so that a good observation image with the speckle noise suppressed can be obtained.

Next, an effect to reduce the speckle interference being attained by having the light source driving circuit 59 change a modulation frequency of the blue semiconductor laser 65 will be described.

Figure 13:
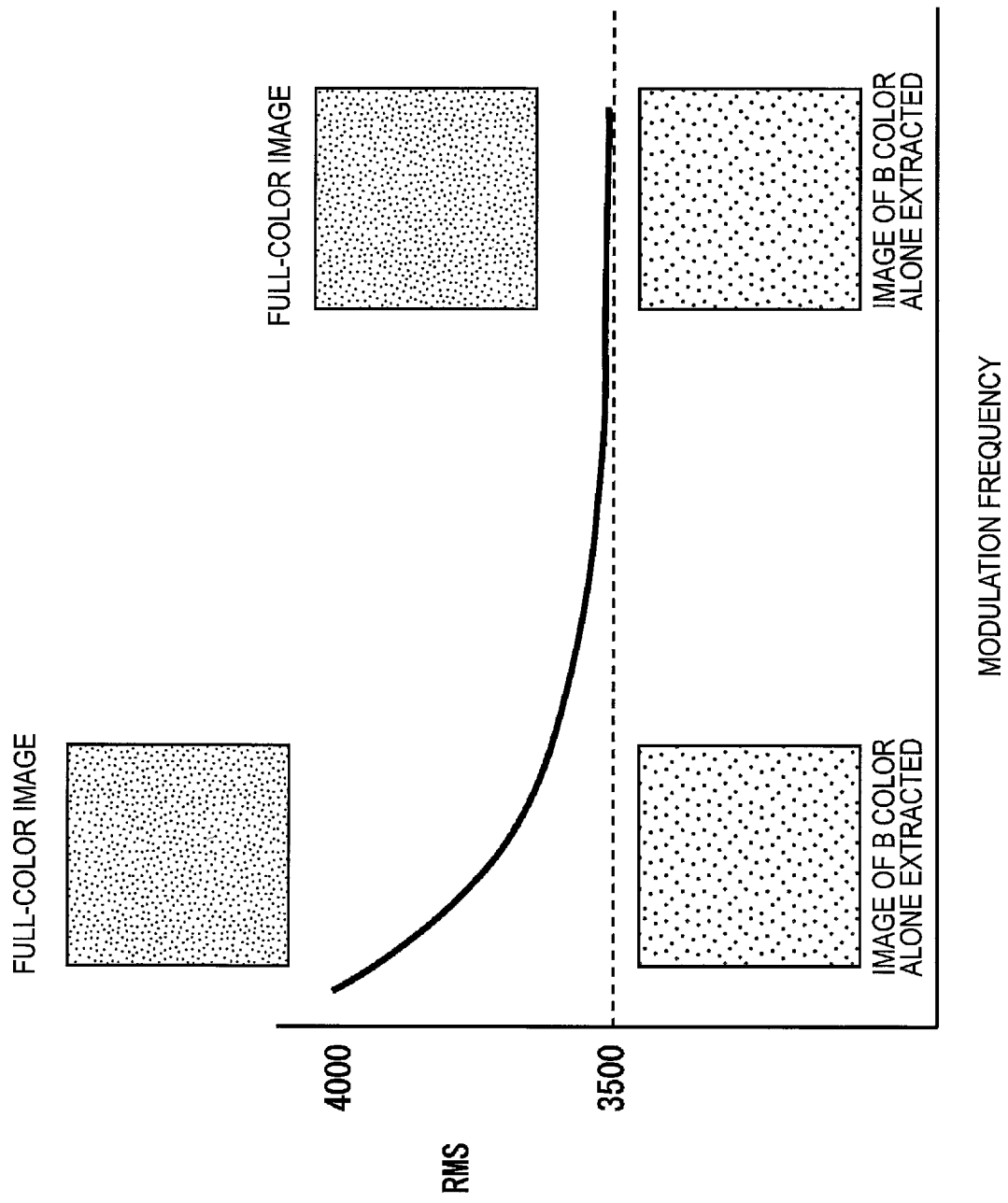
FIG. 13 is a graph illustrating a state of speckle noise, which is obtained by capturing white of the Macbeth chart, against a modulation frequency.

FIG. 13 is a graph illustrating a state of a speckle noise against a modulation frequency when white of the Macbeth chart is captured. In this graph, the abscissa indicates the modulation frequency of the light source driving circuit 59, and the ordinate indicates a root mean square value (RMS value) of pixel values of the captured image. It is assumed in this case that the amplitude of the modulation is in a range of 0 through 100% and that the duty ratio is 50%. Furthermore, the pixel values are values of 16 bits of the RGB colors, and the QL maximum value (quantization level maximum value) is 65416.

In a full color image being captured without the blue semiconductor laser 65 being modulated, a speckle noise having an RMS value of approximately 4000 occurs. Thus, a random noise easily visually recognized is superimposed. The occurrence of this speckle noise derives from the blue laser beam corresponding to the excitation light. When a blue (B) component alone is extracted from the full color image, the speckle noise appears conspicuously.

On the other hand, when the blue semiconductor laser 65 is modulated at a frequency of 1 kHz, the RMS value of the thus captured full color image is lowered to approximately 3500, the light amount distribution is uniform in terms of time and space, and a speckle noise is hardly visually recognized even in an image obtained by extracting a blue component alone. When the modulation frequency is 1 kHz or more, the change of the RMS value against the modulation frequency tends to be reduced and the RMS value is convergent to a prescribed value (which is 3500 in the illustrated exemplary case). Thus, the frequency of approximately 1 kHz is sufficient for attaining the effect to reduce the speckle noise.

Incidentally, although the speckle noise starts to reduce at a modulation frequency of 100 Hz, a capturing period of the imaging device used in an endoscope is, for example, 1/30 through 1/60 second. Hence, if the modulation frequency is approximately 100 Hz, "flicker" would appear in an irradiated area. The "flicker" can be prevented by reducing the modification amplitude, but the speckle noise occurs in this case.

For example, if the modulation amplitude is 100%, an image free from the "flicker" and the speckle noise can be captured at a modulation frequency of 500 Hz or more. If the modulation frequency is 1 kHz or more, the effect is further enhanced, and the occurrence of the speckle noise can be suppressed even if the modulation amplitude is reduced by approximately 10% or 20%. Thus, a more stable noise reducing effect can be attained.

Furthermore, if the light amount of the light source is increased, it is necessary to increase the output of a laser diode in, for example, an endoscope for detailed examination or the like. In this case, the driving current is increased, and in order to drive a large driving current with modulation amplitude of 100%, circuits are required of high matching accuracy, which leads to increase in cost of the power source. In such a case, it is effective to further increase the modulation frequency or reduce the modulation amplitude. This is applied not only to a rectangular pulse shape but also to the aforementioned sine-wave, a saw tooth pulse or a triangular pulse. Furthermore, a similar effect can be attained by sweeping the pulse frequency from 100 Hz to several hundred Hz or several kHz within a charge accumulation time of the capturing period (1/30 through 1/60 second) of the endoscope.

Next, exemplary application of the endoscope system 100 having the aforementioned configuration will be described.

In the application herein described, a shape observation mode for observing an irregular shape on an observed face is provided by utilizing that the level of the occurrence of speckle noise can be freely controlled.

When the white illumination light is emitted from the tip of the inserting section 21 of the endoscope 11 of FIGS. 1 and 2 with the inserting section 21 being inserted into a subject (body cavity), the endoscope system 100 can switch between superimposing of the high frequency signal and not-superimposing of the high frequency signal. Imaging signals obtained through capturing in either case are stored in the memory 63 of FIG. 2. Thereafter, the imaging signal processing section performs appropriate signal processing for the imaging signals for display on the monitor 17 or for storage in a recording medium.

For example, in the case where this endoscope 11 is used for observing a subject under the white illumination light, in normal endoscopic diagnosis, the control section 61 causes the light source driving circuit 59 (see FIG. 2) to apply a driving current on which a high frequency signal is superimposed to the blue semiconductor laser 65 so as to emit a blue laser beam. This blue laser beam is low in coherency. White light having little speckle noise is generated by mixing fluorescence obtained by the wavelength conversion of the phosphor 69 and diffused light diffused by and passing through the phosphor 69.

Alternatively, when the control section 61 stops the superimpose of the high frequency signal supplied from the oscillator 75 of the light source driving circuit 59 onto the driving current, illumination light having a speckle noise is generated. In this case, a captured image including a speckle noise is generated particularly in the blue component (B component). Therefore, an irregular shape on an observed face is clearer in the captured image.

When the control section 61 controls whether or not the high frequency signal is to be superimposed onto the driving current at appropriate timing in this manner, image information suitable for an observation purpose can be selectively obtained from a subject. FIG. 14A is a diagram of a plurality of frame images obtained in a time series by having the imaging optical system capture, and FIG. 14B is an explanatory diagram conceptually illustrating classification of these frame images. In this case, observed images obtained under illumination of white light having little speckle noise and observed images obtained under illumination light having much speckle noise are respectively displayed in different display positions in the monitor 17.

As illustrated in FIG. 14A, the control section 61 controls the emission of the illumination light by the illumination optical system, so that a driving current on which a high frequency signal is superimposed is applied to the blue semiconductor laser 65 to emit a blue laser beam of a center wavelength of 445 nm in a first frame in capturing of a moving image. Thus, a subject is irradiated with white light having little speckle noise. The imaging device 45 captures an image of the subject irradiated with this white light, and the thus obtained imaging signal is stored in the memory 63 (see FIG. 2).

Subsequently, the control section 61 controls the light emitted from the illumination optical system, so that a driving current on which a high frequency signal is not superimposed is applied to the blue semiconductor laser 65 for irradiating the subject with white light including much speckle noise in a second frame. An image of the subject irradiated with this white light is captured, and the thus obtained imaging signal is stored in the memory 63.

Thereafter, similar processing of the irradiation, the imaging and the storage of an imaging signal is repeated, so that the processing for the first frame is performed for a third frame (and other odd-numbered frames) and the processing for the second frame is performed for a fourth frame (and other even-numbered frames). In other words, the irradiation with the white light including little speckle noise and the irradiation with the white light including much speckle noise are alternately switched for every imaging frame of the imaging device 45.

Then, as illustrated in FIG. 14B, the images obtained through irradiation with the white light including little speckle noise and the images obtained through irradiation with the white light including much speckle noise are stored in the memory 63. Image information of these two kinds of imaging signals are respectively displayed in different display areas 78 and 79 in a display screen of the monitor 17 as illustrated in FIG. 15. Although the display areas 78 and 79 have the same size in the exemplary case of FIG. 15, their sizes may be arbitrarily set so that, for example, one of them may be larger than the other or one of them having a smaller size may be displayed to be overlapped inside the display area of the other.

In this manner, normal images obtained under illumination of the normal white light and enhanced images in which the irregular shape is enhanced are simultaneously displayed on one screen. Hence, the state of an observed part may be rapidly and simply grasped. Furthermore, since each image information can be observed on a real-time basis, the image information can be accurately recognized. Hence, the accuracy in diagnosis can be further improved.

Alternatively, the white illumination light including little speckle noise and the white illumination light including much speckle noise may be freely switched therebetween with a simple hand operation of a switch 81 (see FIG. 2) provided on the operating section 19 of the endoscope 11. In this case, the illumination light may be manually switched at arbitrary timing, and hence convenience can be improved.

(Third Configuration)

A third exemplary configuration of the endoscope system will now be described with reference to FIGS. 16 through 20.

In this configuration, the illumination optical system is mechanically vibrated, so as to reduce the speckle noise component Bs to a target value through feedback control.

Figure 16:
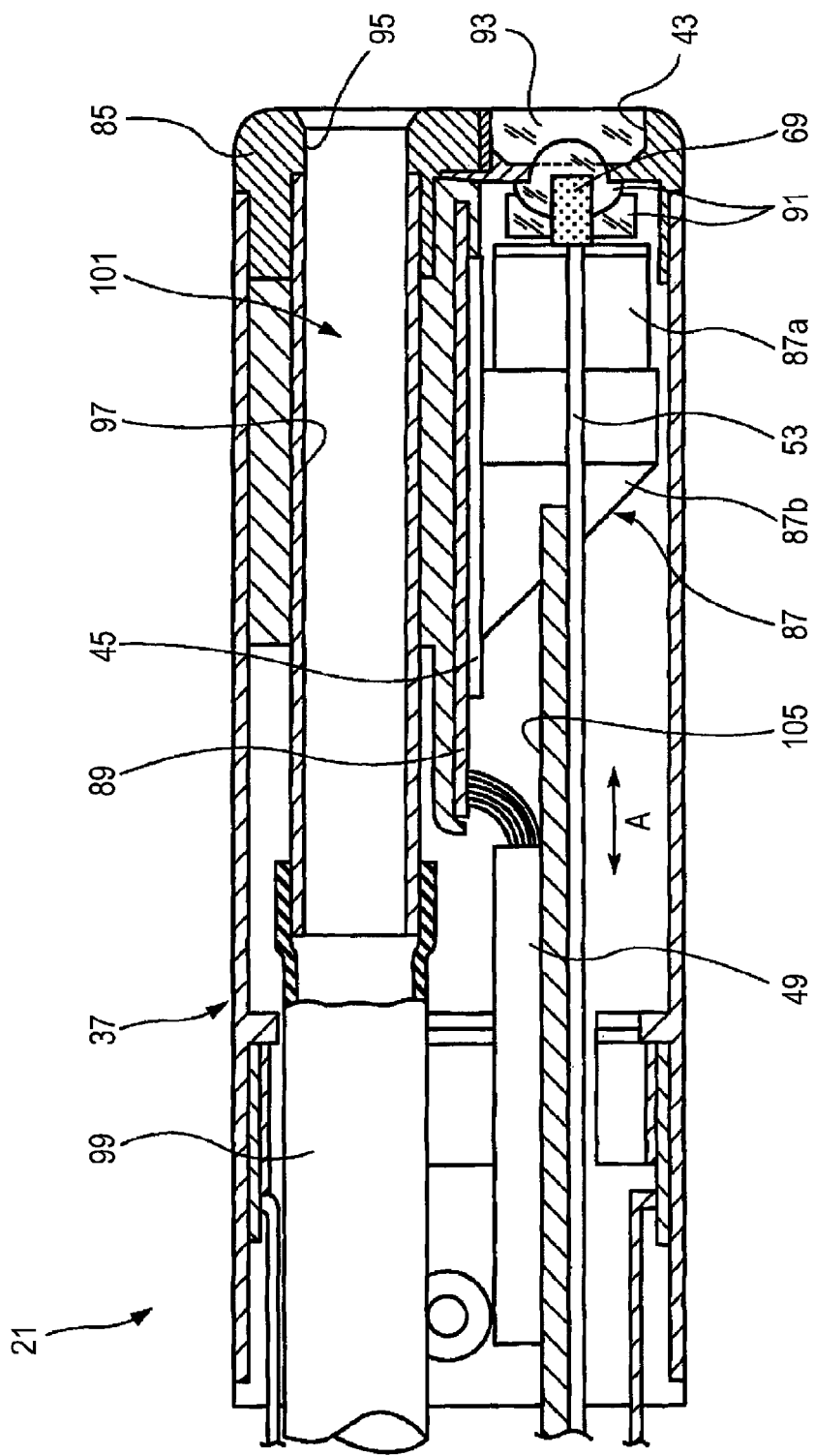
FIG. 16 is a schematic cross-sectional view of a tip portion of an endoscope inserting section of a third configuration.

FIG. 16 is a schematic cross-sectional view of the tip portion of the endoscope inserting section. The tip part 37 of the inserting section 21 is provided with a tip rigid portion 85 made of ceramics or a metal material and is also provided with a member for emitting the illumination light to the light emission window 43 fitted in the tip rigid portion 85. Similarly, a lens barrel 87a housing a condensing optical system of an imaging section 87 is inserted through another hole (not shown) provided in the tip rigid portion 85. The imaging section 87 has a structure in which the optical axis of the lens barrel 87a is bent at right angles by a prism 87b for forming an image on the imaging device 45 mounted on a substrate 89. An imaging signal supplied from the imaging device 45 is sent from the substrate 89 to the processor 15 through the cable 49. The basic colors to which the imaging device 45 has sensitivities may be any of the primary colors RGB or the complementary colors CMY or CMYG.

The illumination optical system is disposed on the front side of the imaging section 87 with respect to the paper of FIG. 16 and includes the phosphor 69 disposed at the light emitting end of the optical fiber 53, a lens group 91 for causing light emitted from the phosphor 69 to outgo toward the tip of the inserting section 21 and a transparent member 93 covering the light emission window 43. The light emitted from the phosphor 69 is made to outgo by the lens group 91 forward along the optical path, so as to illuminate an observed area inside a body cavity through the transparent member 93.

Moreover, an opening 95 is formed in the tip rigid portion 85. A clamp pipe 97 made of a metal is fixed in this opening 95. An end of the clamp pipe 97 on the opposite side to the opening 95 is connected to a tube 99, and the clamp pipe 97 and the tube 99 together form a clamp channel 101. The clamp channel 101 communicates from the opening 95 at the tip of the inserting section 21 to a clamp opening 103 (see FIG. 1) disposed on the operating section 19 side.

A piezoelectric member 105 (an example of a vibration unit) is adhered to the optical fiber 53 disposed on the front side of the phosphor 69, along the axial direction of the optical fiber 53 by a prescribed length. The piezoelectric member 105 may be in the form of a long and narrow sheet to be adhered onto a part of the outer circumference of the optical fiber 53 or may be in the form of a block to be adhered onto the optical fiber 53. By having the optical fiber 53 and the piezoelectric member 105 be closely adhered to each other, distortion of the piezoelectric member 105 caused by application of a voltage is surely propagated to the optical fiber 53 with high efficiency.

Figure 17:
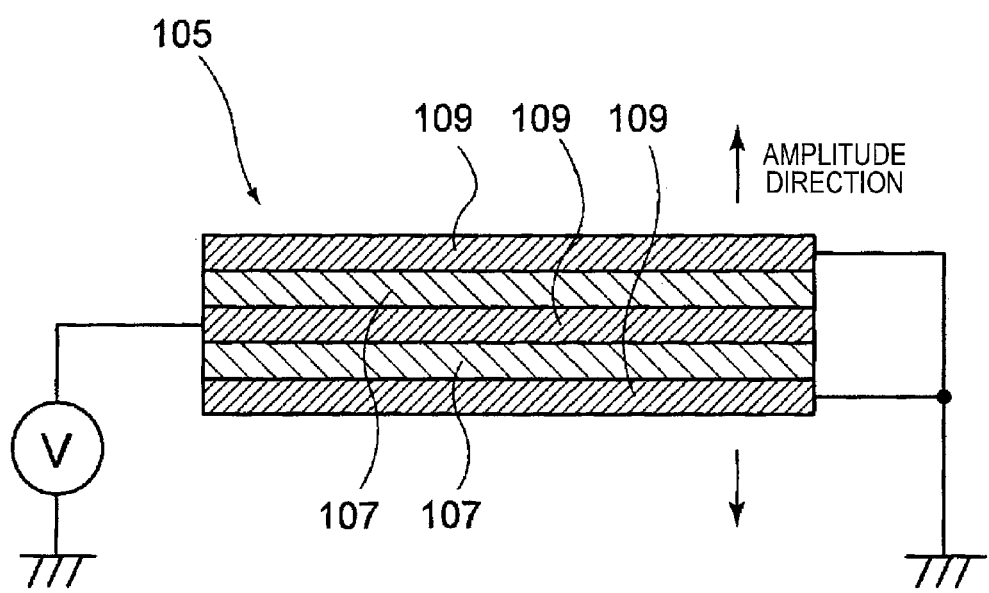
FIG. 17 is an explanatory diagram schematically illustrating a configuration of a piezoelectric member and a driving circuit for the piezoelectric member.

FIG. 17 schematically illustrates the structure of the piezoelectric member 105 and a driving circuit therefor.

The piezoelectric member 105 includes piezoelectric material layers 107 of aluminum nitride or the like sandwiched between electrode layers 109, so that the piezoelectric material layers 107 is distorted by applying an electric field between the electrode layers 109. The piezoelectric member 105 can be adjusted to have an arbitrary vibration frequency by controlling an electric field applying period and a polarity inverting period and can be adjusted to have arbitrary amplitude by controlling an applied voltage. Thus, the piezoelectric member 105 has an advantage of high controllability. Furthermore, with regard to the shape, the piezoelectric member 105 may be made into any of various shapes ranging from a thin shape to a thick shape and may provide a high degree of setting freedom in accordance with a purpose. The piezoelectric material layers 107 may be made of, apart from the aforementioned material, what is called a ferroelectric material such as quartz, lithium niobate, lithium tantalate, langasite, lead zirconate titanate, Rochelle salt, elbaite or poly vinylidene fluoride. It is noted that the electrode layers 109 are connected to the processor 15 through a lead wiring for voltage application (not shown).

The piezoelectric member 105 basically includes the configuration and the driving circuit illustrated in FIG. 17 and causes vibration along an axial direction A (see FIG. 16) with respect to the optical fiber 53. Specifically, the piezoelectric member 105 is closely adhered in such a manner that the direction of stacking the piezoelectric material layers 107 and the electrode layers 109 matches the axial direction of the optical fiber 53. When the piezoelectric member 105 receives a driving voltage signal from the processor 15, the vibration is generated. The driving voltage signal is generated at least in performing the observation. By this vibration, when the laser beam propagated through the optical fiber 53 is emitted from the phosphor 69 as the white illumination light, uneven intensity and speckle noise is prevented in the illumination light. In other words, illumination light with uniform intensity can be obtained with the influence of speckle noise being suppressed. Although the piezoelectric member 105 of FIG. 17 has a five-layered structure as an example, the number of layers may be arbitrarily set.

Furthermore, since the piezoelectric member 105 is disposed on the tip side of the inserting section 21, uneven intensity and speckle noise caused by a biased electric field distribution derived from the optical fiber itself may be prevented from being superimposed again in a part of the optical path anterior to the portion vibrated by the piezoelectric member 105. Moreover, since the aforementioned preventing effect may be attained even if the vibration has a small amplitude, the vibration performance of the piezoelectric member 105 may be suppressed to be minimum, resulting in attaining compactness of the whole apparatus. In addition, since the piezoelectric member 105 is disposed in a position closer to the tip of the inserting section 21 than the bending part 35 where the inserting section 21 is freely bent, even when stress is applied to the optical fiber 53 in bending the bending part 35 and the intensity distribution of propagated light is changed, uniform illumination light can be obtained by the vibration of the piezoelectric member 105 disposed anterior to the bending part 35. Therefore, even if external force is applied to move the inserting section 21, no turbulence is caused in the illumination light, and the observation can be performed always under good illumination light.

As described so far, the effect to reduce the speckle noise can be attained by applying vibration to the optical fiber 53 by the piezoelectric member 105. If the intensity of vibration applied to the optical fiber 53 by the piezoelectric member 105 is feedback controlled so as to minimize the speckle noise component Bs, the speckle noise can be further effectively reduced.

Moreover, with this configuration, since the optical fiber 53 is supported by the piezoelectric member 105 within the inserting section 21, when the inserting section 21 is deformed by an external force during the operation of the endo scope 11, stress concentration in a connecting portion between, for example, the light emitting end of the optical fiber 53 and the phosphor 69 can be prevented. Furthermore, since the piezoelectric member 105 is disposed on the side closer to the tip than the bending part 35, speckle derived from stress applied to the optical fiber 53 in the bending part 35 during the operation of the endoscope, that is, influence of what is called mode change caused in the fiber, can be prevented. It is noted that the piezoelectric member 105 may not be directly contacted with the optical fiber 53 but may be connected to the optical fiber 53 with another intermediate member disposed therebetween. In this case, when the intermediate member is in a shape having a semi-circular groove extending along the outer circumference of the optical fiber 53 or a shape having a through hole for inserting and supporting the optical fiber 53 therein, an contact area with the optical fiber 53 can be increased so as to further increase the contact property and the vibration propagating property.

An alternative modification of the endoscope system having the third configuration will now be described.

Figure 18:
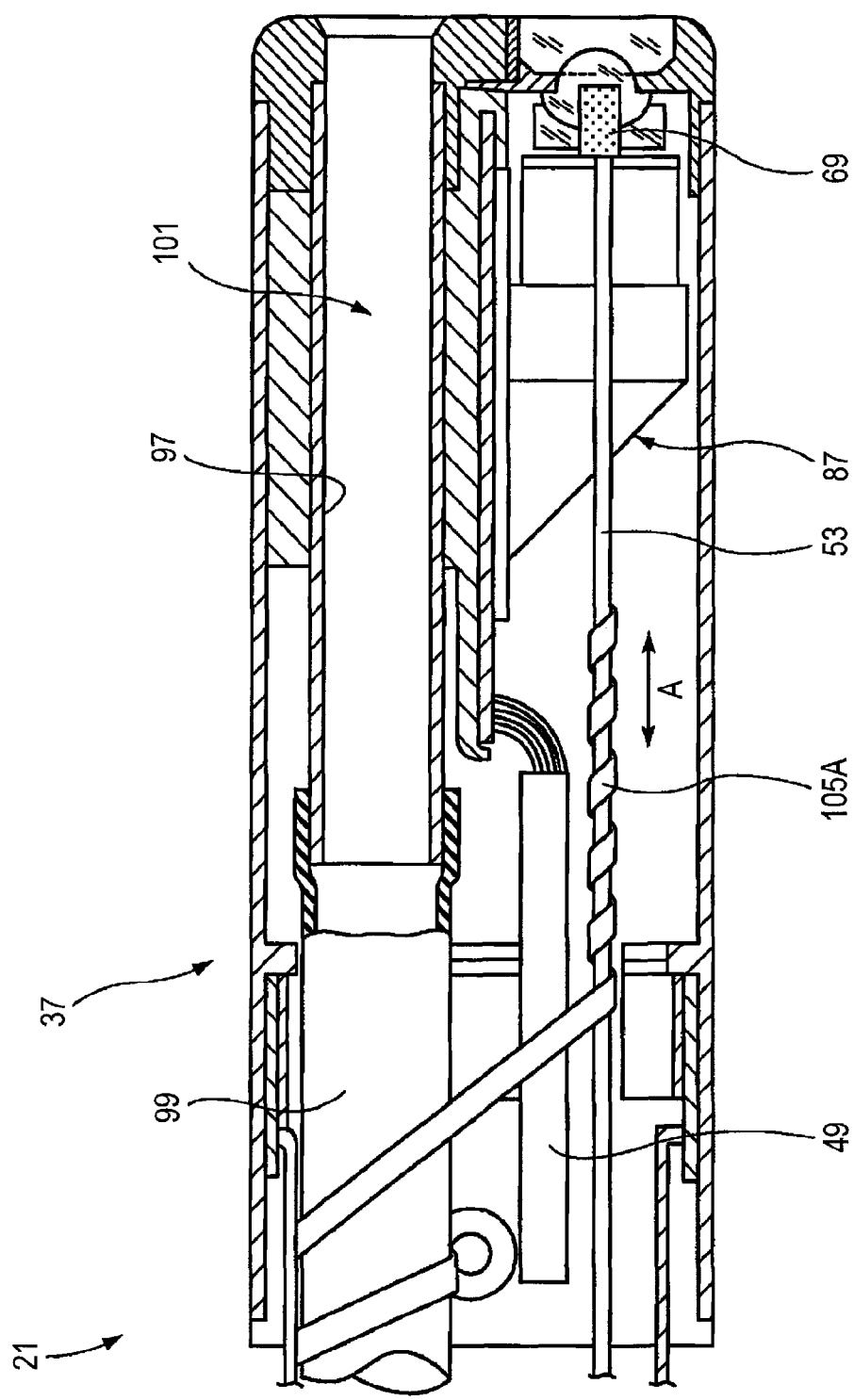
FIG. 18 is a schematic cross-sectional view of a tip of the endoscope inserting section in which a piezoelectric member is wound around an optical fiber.

FIG. 18 is a schematic cross-sectional view of the tip of the endoscope inserting section in which a piezoelectric member is wound around an optical fiber. Herein, the description of elements which are the same as those illustrated in FIG. 16 will be omitted or simplified. As illustrated in FIG. 18, the piezoelectric member 105A in the shape of a flexible tape is helically wound around and adhered to the optical fiber 53 in the tip part of the inserting section 21. In this case, the vibration generated by the piezoelectric member 105A causes, in the optical fiber 53, twisting vibration including vibration along the axial direction A. In other words, the tape-shaped piezoelectric member 105A generates vibration having an amplitude direction along its lengthwise direction, so that the optical fiber 53 can be vibrated along the axial direction A while twisting due to contraction and expansion along the axial direction A. Since the optical fiber 53 is supported in a hanging state by the piezoelectric member 105A and is vibrated, a larger amplitude can be attained with smaller vibration energy.

Furthermore, the tip side of the piezoelectric member 105A is helically wound around the optical fiber 53 as described above, and its rear end side is wound around and fixed to the tube 99 of the clamp channel 101. Since the rear end side of the piezoelectric member 105A is thus adhered and fixed to the tube 99, the piezoelectric member 105A can be connected to the optical fiber 53 having a small diameter so as not to be largely affected by an external force. Hence, the piezoelectric member 105A can be continuously stably connected to the optical fiber 53. It is noted that a lead wiring for voltage application is connected to the electrode layer 109 of the piezoelectric member 105A, so as to supply a driving signal from the processor 15 to the piezoelectric member 105A.

When this configuration in which the tape-shaped piezoelectric member 105A is wound around the optical fiber 53 is employed, since the whole outer circumference of the optical fiber 53 can be uniformly expanded and contracted, the occurrence of uneven intensity and speckle noise can be prevented over an entire irradiated face with high accuracy. Hence, illumination light having a more uniform light amount distribution can be irradiated.

Moreover, since the optical fiber 53 is supported in the hanging state within the inserting section 21, the optical fiber 53 is slightly bent by an external force applied to the inserting section 21, and this bending deformation also reduces the occurrence of uneven intensity and speckle noise in the illumination light.

Still another modification of the endoscope system having the third configuration will now be described.

Figure 19:
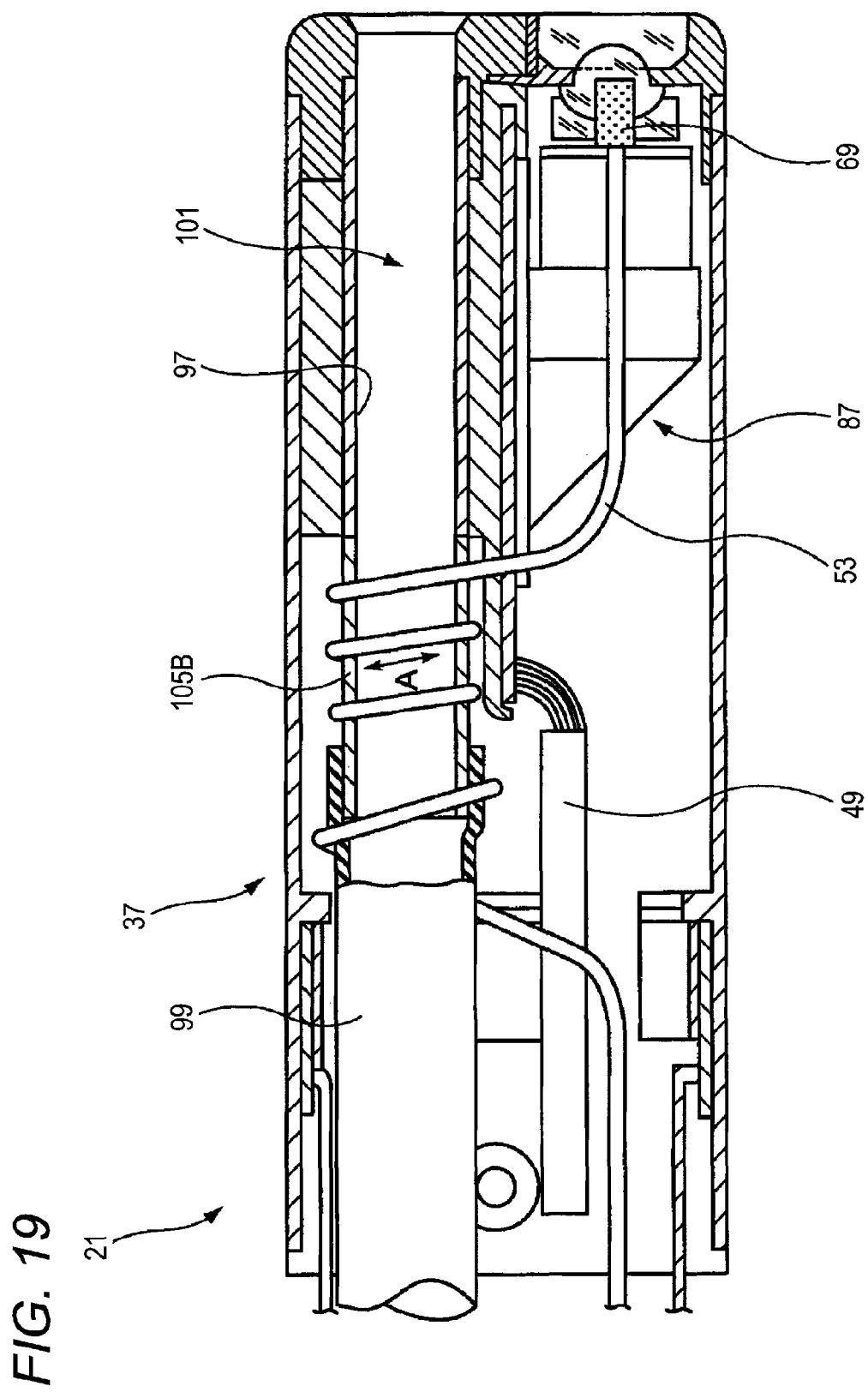
FIG. 19 is a schematic cross-sectional view of the tip of the endoscope inserting section in which an optical fiber is wound around a clamp channel.

FIG. 19 is a schematic cross-sectional view of the tip of the endoscope inserting section in which an optical fiber is wound around a clamp channel. Herein, the description of the elements which are the same as those illustrated in FIG. 16 will be omitted or simplified.

As illustrated in FIG. 19, in the tip part of this inserting section 21, a connecting portion between the tube 99 and the clamp pipe 97 of FIG. 16 is formed of a tubular piezoelectric member 105B having inner and outer diameters substantially the same as those of the clamp pipe 97. The tubular piezoelectric member 105B has one end brought into contact with and connected to the clamp pipe 97 and the other end connected to the tube 99, so as to serve as a part of the clamp channel 101.

The tubular piezoelectric member 105B generates vibration for repeating expansion and contraction in diameter. When the optical fiber 53 is wound around this piezoelectric member 105B and fixed with an adhesive or the like, the vibration generated by the piezoelectric member 105B is propagated to the optical fiber 53. Thus, the optical fiber 53 is vibrated along the axial direction A. As illustrated, when the optical fiber 53 is made up into a bundle and wound repeatedly (for example, wound along the axial direction of the clamp channel 101 plural times), the occurrence of uneven intensity and speckle noise can be prevented by a synergetic effect. In particular, when a direction along a winding face of the repeated winding, namely, the axial direction of the optical fiber 53, matches the vibration direction, the light intensity attained on an irradiated face can be made uniform with high efficiency.

When the optical fiber 53 is wound around the tubular piezoelectric member 105B, the optical fiber 53 may be wound so as to cross itself on the piezoelectric member 105B. In this case, a pressing force is applied to the crossing optical fiber 53. The thus generated compression stress (strain) changes the refractive index, resulting in further increasing the effect to attain uniform intensity of the illumination light. Furthermore, when the optical fiber 53 is wound around the piezoelectric member 105B while squeezing tightly so as to allow tensile stress to remain in the optical fiber 53 after the winding and is fixed with an adhesive or the like with the tension applied, the effect to attain uniform light intensity can be also enhanced.

The piezoelectric member 105B may be provided to surround the clamp pipe 97 so as to form a double tubular structure or may be provided on the outer circumference of the clamp pipe 97 in a part along the circumferential direction, instead of providing as a part of the clamp pipe 97 included in the clamp channel 101 as described above.

In the endoscope system 100 described so far, since the optical fiber 53 for guiding a laser beam to the phosphor 69 disposed at the tip of the inserting section 21 is vibrated on the tip side within the inserting section 21, the light intensity distribution of the illumination light emitted from the phosphor 69 can be made uniform. Specifically, the uneven intensity and speckle noise of the laser beam itself are reduced, and in addition, since the optical fiber 53 is vibrated in a portion in the vicinity of the light emitting end, the uneven intensity and speckle noise caused by a biased electric field distribution derived from the optical fiber 53 itself can be prevented from being superimposed on the guided laser beam in a part disposed between the vibrated portion and the light emitting end positioned anterior to the vibrated portion in the optical path.

The position of the piezoelectric member 105, 105A, 105B is preferably close to the tip of the inserting section 21 as much as possible and is between the light emitting end of the optical fiber 53 and the operating section 19. In particular, the piezoelectric member 105, 105A, 105B is disposed preferably within 2 m and more preferably within 1 m from the light emitting end. In other words, the vibration unit is disposed within 2 m from the light emitting end of the optical fiber 53 toward the base side of the inserting section 21 opposite to the tip side.

The vibration unit, which vibrates the optical fiber 53, is not limited to the aforementioned piezoelectric member 105, 105A, 105B but may be any of compact and remote controllable vibration sources of various types including a electrodynamic type such as a voice coil motor, a hydraulic type employing piston driving, an unbalance mass type, and the like.

Furthermore, as a preferable vibration generating condition of the vibration unit, a vibration frequency is preferably several times through several ten times as high as a frame frequency in capturing an image by the imaging device 45 (see FIG. 16). Furthermore, when a large amplitude is caused in capturing an image, heat may be generated in the tip part of the inserting section 21. When the amplitude is insufficient, the effect to reduce noise in the illumination light is reduced. Therefore, it is necessary to suppress also the amplitude within a prescribed range.

For example, assuming that a multimode optical fiber having a core diameter of 30 through 116 μm is employed and that the emission wavelength of the laser beam is 375 through 850 nm, the amplitude of the vibration unit is preferably 0.001 through 0.1 mm and the vibration frequency is preferably 50 through 100 Hz. Furthermore, assuming that the degree of vibration is expressed by using acceleration, it is preferably in a range of, for example, 0.1 G (corresponding to an amplitude of 0.01 mm and a vibration frequency of 50 Hz) to 5 G.

If the core diameter of the optical fiber is smaller than 30 μm, the lens coupling efficiency to the optical fiber would be lowered because the width of the light emitting portion of the semiconductor laser is approximately 10 through 30 μm, and the optical fiber would be too sensitive to the position accuracy. Furthermore, a ferrule used in a general connector has an inner diameter of 125 μm, and the outer diameter of the optical fiber including the clad layer is preferably not more than the inner diameter of the ferrule. Accordingly, since the clad layer has a thickness of at least several μm, the core diameter of the optical fiber is preferably 116 μm or less.

A measurement result of evenness of the illumination light obtained with the configuration using the vibration unit of FIG. 16 will now be described.

Figure 20:
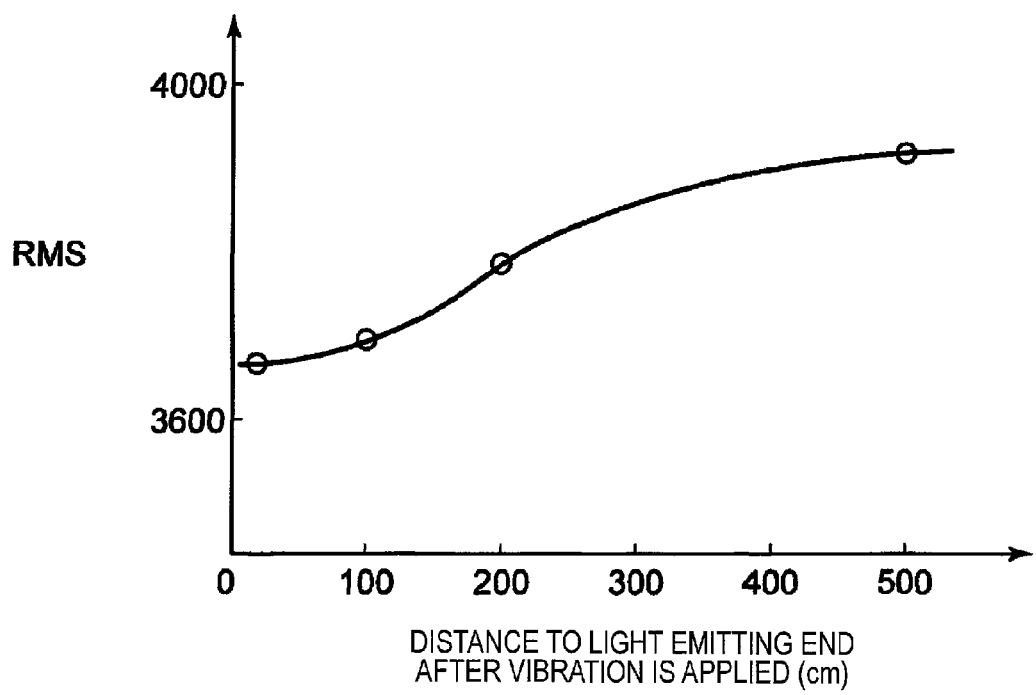
FIG. 20 is a graph illustrating a relationship between a distance from a vibration unit to a light emitting end obtained after vibration is applied, which is indicated in the abscissa, and an RMS value corresponding to a noise of illumination light, which is indicated in the ordinate.

FIG. 20 is a graph illustrating a relationship between a distance from the vibration unit to the light emitting end after vibration is applied, which is indicated by the abscissa, and the RMS value corresponding to noise of the illumination light, which is indicated by the ordinate. The vibration applied to the optical fiber is set to a vibration frequency of 500 Hz and an amplitude of 0.001 mm. As illustrated in FIG. 20, when the distance from the vibration unit to the light emitting end exceeds 100 cm, the increase ratio of noise of the illumination light is increased. Also, the noise is continuously increased after the distance is increased beyond 200 cm up to 500 cm.

When the RMS value is approximately 3700, noise of the illumination light is insignificant. When the RMS value becomes approximately 3900, noise would be clearly recognized visually. Therefore, the RMS value is preferably suppressed to 3800 or less. It is noted that the RMS value is a numerical value obtained with being defined as a root mean square value of an extracted single color of an RGB 16-bit values of a captured image (i.e., an RMS value obtained when the QL maximum value is 65416).

Incidentally, if the speckle noise remains after the speckle noise reducing processing such as the superimpose of the high frequency signal on the driving current to be supplied to the laser light source, which is described in the second configuration, or the application of vibration to the optical fiber, which is described in the third configuration, the speckle noise removing processing described in the first configuration may be further performed in addition to the speckle noise reducing processing.

The present invention is not limited to the above-described embodiments but it is to be understood by those skilled in the art that various changes and modifications may be made in the invention without departing from the spirit and scope thereof As described in detail so far, the following are at least described:

(1) According to an aspect of the invention, an endoscope system captures an image of a subject under illumination light including a laser beam by an imaging device having sensitivities to a plurality of basic color components, performs image processing for the captured image and outputs the resultant image as an observation image. The captured image includes a first basic color component on which a speckle noise of the laser beam is superimposed and a second basic color component not including the speckle noise. The endoscope system includes a speckle noise extracting unit and a controller. The speckle noise extracting unit extracts a speckle noise component based on difference information between the first basic color component and the second basic color component. The controller determines a control amount for removing the speckle noise component from the first basic color component based on the extracted speckle noise component.

With this endoscope system, the speckle noise component is extracted based on the difference information between the first basic color component and the second basic color component. The speckle noise is removed by using this speckle noise component as an evaluation parameter. Therefore, the speckle noise, which has been difficult to quantitatively evaluate, can be controlled using the evaluation parameter, so that a control amount for removing the speckle noise can be optimally set. Accordingly, in removing the speckle noise, it is not necessary to perform useless control, excessive calculation and the like. Thus, the speckle noise can be optimally removed with high efficiency. As a result, a good observation image free from flicker and unevenness peculiar to laser can be always stably obtained.

(2) In the endoscope system of (1), wherein the speckle noise extracting unit may extract the speckle noise component for each pixel of the captured image by dividing the first key color component of each pixel by the second key color component of each pixel.

With this endoscope system, an image of the first basic color component including the speckle noise component is divided by an image of the second basic color component not including the speckle noise component, so as to extract feature quantity in which the first and second basic color components are different, namely, so as to extract change in brightness caused by the speckle noise. Thus, the speckle noise component can be obtained.

(3) In the endoscope system of any one of (1) to (2), the basic color components may include three primary colors of red, green and blue. The speckle noise extracting unit may extract the speckle noise component based on difference information between a B component corresponding to the first basic color component of the captured image and a G component corresponding to the second basic color component.

With this endoscope system, since a laser beam of a short wavelength includes the speckle noise, the speckle noise can be extracted by obtaining difference information between the B component and a color component other than the B component. Furthermore, when the G component, which has comparatively high brightness among the three colors, is used, noises other than the speckle noise are hardly caused in obtaining the difference from the B component. Hence, the speckle noise can be accurately obtained.

(4) In the endoscope system of any one of (1) to (2), the basic color components may include three complementary colors of cyan, magenta and yellow. The endoscope system may further include a color converting unit that obtains, through calculation, a B component corresponding to the first basic color component and a G component corresponding to the second basic color component based on a C component, an M component and a Y component of the captured image. The speckle noise extracting unit may extract the speckle noise component based on difference information between the B component obtained through the calculation and the G component obtained through the calculation.

With this endoscope system, the B component and the G component are obtained by the color converting unit after the complementary color components are detected. Therefore, the speckle noise can be extracted based on difference information therebetween.

(5) In the endoscope system of any one of (1) to (2), the basic color components may include four complementary colors of cyan, magenta, yellow and green. The endoscope system may further include a color converting unit that obtains, through calculation, a B component corresponding to the first basic color component based on a C component, an M component and a Y component of the captured image. The speckle noise extracting unit may extract the speckle noise component based on difference information between the B component obtained through the calculation and a G component of the captured image.

With this endoscope system, the B component is obtained by the color converting unit after the complementary color components are detected. The speckle noise component can be extracted based on the difference information from the G component of the captured image.

(6) In the endoscope system of any one of (1) to (5), the controller may generate the observation image by subtracting the speckle noise component of each pixel from the first basic color component of each pixel.

With this endoscope system, the speckle noise component superimposed on the first basic color component can be removed through the subtraction.

(7) The endoscope system of any one of (1) to (6) may further include a lighting apparatus and a high frequency superimposing unit. The lighting apparatus includes a laser light source, a phosphor, and an optical fiber. The laser light source emits light of a first wavelength band. The phosphor emits light of a second wavelength band through excitation emission caused by the light of the first wavelength band. The optical fiber guides the light of the first wavelength band from the laser light source to the phosphor for irradiation. The lighting apparatus may generate the illumination light by mixing the light of the first wavelength band and the light of the second wavelength band. The high frequency superimposing unit superimposes a high frequency signal on a driving current to be supplied to the laser light source for attaining multimode oscillation of the laser light source. The controller may feedback control the high frequency signal for minimizing an intensity parameter of the speckle noise component.

With this endoscope system, since the driving current on which the high frequency signal is superimposed is applied to the laser light source, the longitudinal mode is changed to multimode, and each of a plurality of lateral modes attains distribution of the wavelength. Also, the lateral modes are changed with respect to the time axis. Therefore, light having little speckle interference can be always stably emitted. Accordingly, the speckle noise can be prevented from occurring in an irradiated area. Furthermore, when the high frequency signal to be superimposed on the driving current for the laser light source is feedback controlled, the speckle noise component can be minimized.

(8) The endoscope system of any one of (1) to (6) may further include a lighting apparatus and a vibration unit. The lighting apparatus includes a laser light source, a phosphor, and an optical fiber. The laser light source emits light of a first wavelength band. The phosphor emits light of a second wavelength band through excitation emission caused by the light of the first wavelength band. The optical fiber guides the light of the first wavelength band from the laser light source to the phosphor for irradiation. The lighting apparatus may generate the illumination light by mixing the light of the first wavelength band and the light of the second wavelength band. The vibration unit is disposed inside an endoscope inserting section and vibrates the optical fiber in a direction along an axial direction. The controller may feedback control a vibration intensity of the vibration unit for minimizing an intensity parameter of the speckle noise component.

With this endoscope system, since the optical fiber disposed inside the endoscope inserting section is vibrated by the vibration unit, occurrence of uneven intensity and speckle noise in the illumination light can be prevented, so as to obtain a good observation image not disturbing observation of a diseased part. Furthermore, when the intensity of vibration applied by the vibration unit is feedback controlled, the speckle noise component can be minimized.

What is claimed is:

1. An endoscope system that captures an image of a subject under illumination light including a laser beam by an imaging device having sensitivities to a plurality of basic color components, performs image processing for the captured image and outputs the resultant image as an observation image, wherein the captured image includes a first basic color component on which a speckle noise of the laser beam is superimposed and a second basic color component not including the speckle noise, the endoscope system comprising:

a speckle noise extracting unit that extracts a speckle noise component based on difference information between the first basic color component and the second basic color component; and a controller that determines a control amount for removing the speckle noise component from the first basic color component based on the extracted speckle noise component.

2. The endoscope system according to claim 1,
wherein the speckle noise extracting unit extracts the speckle noise component for each pixel of the captured image by dividing the first key color component of each pixel by the second key color component of each pixel.

3. The endoscope system according to claim 1,
wherein the basic color components include three primary colors of red, green and blue, and
the speckle noise extracting unit extracts the speckle noise component based on difference information between a B component corresponding to the first basic color component of the captured image and a G component corresponding to the second basic color component.

4. The endoscope system according to claim 1,
wherein the basic color components include three complementary colors of cyan, magenta and yellow,
the endoscope system further comprises a color converting unit that obtains, through calculation, a B component corresponding to the first basic color component and a G component corresponding to the second basic color component based on a C component, an M component and a Y component of the captured image, and
the speckle noise extracting unit extracts the speckle noise component based on difference information between the B component obtained through the calculation and the G component obtained through the calculation.

5. The endoscope system according to claim 1,
wherein the basic color components include four complementary colors of cyan, magenta, yellow and green,
the endoscope system further comprises a color converting unit that obtains, through calculation, a B component corresponding to the first basic color component based on a C component, an M component and a Y component of the captured image, and
the speckle noise extracting unit extracts the speckle noise component based on difference information between the B component obtained through the calculation and a G component of the captured image.

6. The endoscope system according to claim 1,
wherein the controller generates the observation image by subtracting the speckle noise component of each pixel from the first basic color component of each pixel.

7. The endoscope system according to claim 1, further comprising:
a lighting apparatus that includes
a laser light source that emits light of a first wavelength band,
a phosphor that emits light of a second wavelength band through excitation emission caused by the light of the first wavelength band, and
an optical fiber that guides the light of the first wavelength band from the laser light source to the phosphor for irradiation, the lighting apparatus generating the illumination light by mixing the light of the first wavelength band and the light of the second wavelength band; and a high frequency superimposing unit that superimposes a high frequency signal on a driving current to be supplied to the laser light source for attaining multimode oscillation of the laser light source, wherein the controller feedback controls the high frequency signal for minimizing an intensity parameter of the speckle noise component.

8. The endoscope system according to claim 1, further comprising:

a lighting apparatus that includes a laser light source that emits light of a first wavelength band, a phosphor that emits light of a second wavelength band through excitation emission caused by the light of the first wavelength band, and an optical fiber that guides the light of the first wavelength band from the laser light source to the phosphor for irradiation, the lighting apparatus generating the illumination light by mixing the light of the first wavelength band and the light of the second wavelength band; and a vibration unit that is disposed inside an endoscope inserting section and vibrates the optical fiber in a direction along an axial direction, wherein the controller feedback controls a vibration intensity of the vibration unit for minimizing an intensity parameter of the speckle noise component.

* * * * *